(12) United States Patent
Arimoto et al.

(10) Patent No.: US 8,772,497 B2
(45) Date of Patent: Jul. 8, 2014

(54) METHOD FOR PRODUCING 1, 2-DIHYDROPYRIDINE-2-ONE COMPOUND

(75) Inventors: Itaru Arimoto, Tokyo (JP); Satoshi Nagato, Tokyo (JP); Yukiko Sugaya, Tsukuba (JP); Yoshio Urawa, Kamisu (JP); Koichi Ito, Tsukuba (JP); Hiroyuki Naka, Kamisu (JP); Takao Omae, Tsukuba (JP); Akio Kayano, Kamisu (JP); Katsutoshi Nishiura, Kamisu (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 315 days.

(21) Appl. No.: 12/870,507

(22) Filed: Aug. 27, 2010

(65) Prior Publication Data

US 2010/0324297 A1 Dec. 23, 2010

Related U.S. Application Data

(60) Division of application No. 11/649,299, filed on Jan. 4, 2007, now Pat. No. 8,304,548, which is a continuation-in-part of application No. PCT/JP2005/012364, filed on Jul. 5, 2005, and a continuation-in-part of application No. PCT/JP2005/012388, filed on Jul. 5, 2005.

(30) Foreign Application Priority Data

Jul. 6, 2004 (JP) ................. 2004-198709

(51) Int. Cl.
*C07D 401/04* (2006.01)
(52) U.S. Cl.
USPC ....................................... 546/257
(58) Field of Classification Search
None
See application file for complete search history.

(56) References Cited

U.S. PATENT DOCUMENTS

| 6,133,255 A | 10/2000 | Harrison et al. |
| 2004/0023973 A1 | 2/2004 | Nagato et al. |

FOREIGN PATENT DOCUMENTS

| CN | 1436172 A | 8/2003 |
| DE | 19643037 A1 | 4/1998 |
| EP | 0802195 A2 | 10/1997 |
| EP | 1300396 A1 | 4/2003 |
| EP | 2053041 A2 | 4/2009 |
| EP | 2177520 A1 | 4/2010 |
| IN | 238440 | 2/2010 |
| JP | 52-083761 | 7/1977 |
| JP | 55-031072 | 3/1980 |
| JP | 2005-515995 A | 6/2005 |
| WO | WO 94/25469 A1 | 11/1994 |
| WO | WO 95/01357 A1 | 1/1995 |
| WO | WO 96/10023 A1 | 4/1996 |
| WO | WO 96/33974 A1 | 10/1996 |
| WO | WO 97/18163 A1 | 5/1997 |
| WO | WO 97/28135 A1 | 8/1997 |
| WO | WO 97/34878 A1 | 9/1997 |
| WO | WO 97/43276 A1 | 11/1997 |
| WO | WO 98/38173 A1 | 9/1998 |
| WO | WO 98/50384 A1 | 11/1998 |
| WO | WO 98/55480 A1 | 12/1998 |
| WO | WO 99/31062 A1 | 6/1999 |
| WO | WO 00/01376 A2 | 1/2000 |
| WO | WO 00/07988 A1 | 2/2000 |
| WO | WO 01/96308 A1 | 12/2001 |
| WO | WO 03/047577 A2 | 6/2003 |

OTHER PUBLICATIONS

Richard A. Earl et al'; Journal of Organic Chemistry, vol. 49, pp. 4786-4800, 1984.*
The Voluntary Argument and the Amendment for Chinese Patent Application No. 201010246226.1, with English translation (Dec. 15, 2011).
Amendment filed on Dec. 15, 2011 in corresponding Chinese Patent Application No. 201010246226.1, with English translation (Jan. 1, 2012).
Office Action dated Dec. 31, 2011 which issued in corresponding Chinese Patent Application No. 201010246226.1, with English translation.
Notice of Allowance dated Jan. 13, 2012 issued in corresponding Chinese Patent Application No. 200580011565.9 (with English translation).
Response to the Chinese Office Action filed on Feb. 22, 2012, for Application No. 201010246226.1 with the English translation.
Notice of Allowance issued on Feb. 9, 2012 in counterpart Chinese patent application No. 200910138575.9.
Communication for European Application No. 05758232.2, dated May 14, 2012.

(Continued)

*Primary Examiner* — Zinna Northington Davis
(74) *Attorney, Agent, or Firm* — Birch, Stewart, Kolasch & Birch, LLP

(57) ABSTRACT

The present inventions provide a method for commercially producing a 1,2-dihydropyridine-2-one compound represented by the following formula (III-a)

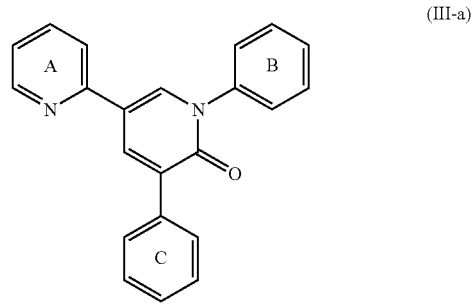

(III-a)

wherein the ring A represents an optionally substituted 2-pyridyl group, the ring B represents an optionally substituted phenyl group, and the ring C represents an optionally substituted phenyl group. Further, the invention provides crystals of 3-(2-cyanophenyl)-5-(2-pyridyl)-1-phenyl-1,2-dihydropyridin-2-one and production processes therefore.

26 Claims, 12 Drawing Sheets

(56) References Cited

OTHER PUBLICATIONS

Request to record the extended patent application dated May 29, 2012, for Macau Application No. J/000789(395).
Communication dated Aug. 2, 2012 from counterpart Brazilian Patent Application No. PI0510254-5 (English translation is attached).
Submission Documents dated Aug. 9, 2012 Before the European Patent Office for counterpart European Application No. 05 758 232.2.
Notice of Allowance dated Mar. 9, 2012 for Mexican Patent Application No. PA/a/2006/014458 (English translation is attached).
Japanese Office Action for Application No. 2007-009518 dated Aug. 16, 2011, with English translation thereof and English translation of Claims for Japanese Application No. 2007-009518.
Alan Nadin et al.; Synthesis of Tricyclic Pyridones by Radical Cyclization, Tetrahedron Letters, vol. 40, No. 21, pp. 4073-4076 (1999).
Alex Gray et al.; Neuroscience Letters, vol. 268, pp. 127-130 (1999).
Brian Meldrum; Brain Research Reviews, vol. 18, pp. 293-314 (1993).
C. Arias et al.; Journal of Neuroscience Research, vol. 41, pp. 561-566 (1995).
Evan B. Dreyer et al.; European Journal of Neuroscience, vol. 7, pp. 2502-2507 (1995).
Gissot et al., "A Functionalized, Deep Cavitand Catalyzes the Aminolysis of a Choline Derivative" Journal of the American Chemical Society, vol. 126, No. 24, 2004, pp. 7424-7425, XP002522905.
Helene Hardin-Pouzet et al.; GLIA, vol. 20, pp. 79-85 (1997).
Hiroshi Ushijima et al.; European Journal of Neuroscience, vol. 7, pp. 1353-1359 (1995).
Ibrahim El-Sayed El-Kholy; J. Chem. Soc., pp. 4490-4498 (1961).
Jang-Ho J. Cha et al.; Neuroscience Letters, vol. 132, pp. 55-58, 1991.
Japanese Notification of Reason for Rejection mailed Jun. 11, 2010, for corresponding Japanese Application No. 2006-528897.
Jolanta Kotlinski et al.; Pharmacology Biochemistry and Behavior, vol. 60, No. 1, pp. 119-124 (1998).
Jose Castillo et al.; The Lancet, vol. 349, pp. 79-83 (1997).
Kaczmarek et al., "Bulletin of the Polish Academy of Sciences", Beilstein Institite for Organic Chemistry, (Jan. 2009), vol. 32, No. 3-6, pp. 105-114, XP-002522906.
Lechoslaw Turski et al.; Journal of Pharmacology and Experimental Therapeutics, vol. 260, No. 2, pp. 742-747 (1992).
Lorise C. Gahring et al.; Neurology, vol. 48, pp. 494-500 (1997).
Malcolm J. Sheardown et al.; Science, vol. 247, pp. 571-574 (1990).
Mehul B. Thathagar et al., J. Amer. Chem. Soc., 124(40), 2002, pp. 11858-11859.
Mitsuharu Yoshiyama et al.; The Journal of Pharmacology and Experimental Therapeutics, vol. 280, No. 2, pp. 894-904 (1997).
P. Sindou et al.; Journal of Neurological Sciences, vol. 126, pp. 133-137 (1994).
Paul A. Rosenberg et al.; Proc. Natl. Acad. Sci., vol. 88, pp. 4865-4869 (1991).
Pessolano et al., "Novel Nucleophilic Substitution of Alkyl Bromo-2(1H)-pyridones", Journal of Heterocyclic Chemistry, vol. 22, 1985, XP-002522914, pp. 265-272.
Reiko Fujita et al.; Studies on 1-Alkyl-2(1H)-pyridone Derivatives XXXII. The Friedel-Crafts Reaction of 1-Alkyl-2(1H)-pyridone Derivatives with Acid Anhydride; Yagugaku Zasshi, vol. 110, No. 6, pp. 449-452 (1990).
Rossella Brusa et al.; Science, vol. 270, pp. 1677-1680 (1995).
Stuart A. Lipton; Neurology, vol. 42, pp. 1403-1405 (1992).
Thomas J. Nelson et al.; Proc. Natl. Acad. Sci., vol. 87, pp. 269-273 (1990).
Trisha Spencer Smith et al.; Neuroreport, vol. 5, pp. 1009-1011 (1994).
Werner E.G. Muller et al.; European Journal of Pharmacology, vol. 226, pp. 209-214 (1992).
Haleblian et al., "Pharmaceutical Applications of Polymorphism," Journal of Pharmaceutical Sciences, vol. 58, No. 8, Aug. 1969, pp. 911-929.
Mirza et al., "Influence of Solvents on the Variety of Crystalline Forms of Erythromycin," AAPS PharmSci, vol. 5, No. 2, Article 12, Apr. 14, 2003, pp. 1-9.
Office Action (date of dispatch: unknown) for Egyptian Application No. 1270/2006 in review of a response dated Mar. 3, 2010.
Australian Amendment, filed Dec. 18, 2006, for Australian Patent Application No. 2005258385.
Australian Notice of Acceptance, dated Oct. 27, 2009, for Australian Patent Application No. 2005258385.
Australian Office Action, dated Jul. 10, 2009, for Australian Patent Application No. 2005258385.
Australian Office Action, dated Nov. 3, 2008, for Australian Patent Application No. 2005258385.
Australian Response to Office Action, filed Jun. 10, 2009, for Australian Patent Application No. 2005258385.
Australian Response to Office Action, filed Sep. 14, 2009, for Australian Patent Application No. 2005258385.
Bangladeshi Examination Report, dated Feb. 28, 2007, for Bangladeshi Patent Application No. 147/2005.
Bangladeshi Notice of Allowance, dated May 8, 2007, for Bangladeshi Patent Application No. 147/2005.
Bangladeshi Notice of Allowance, dated May 8, 2007, for Bangladeshi Patent Application No. 47/2007.
Bangladeshi Response to Examination Report, filed Mar. 7, 2007, for Bangladeshi Patent Application No. 147/2005.
Canadian Amendment After Allowance, filed Aug. 25, 2009, for Canadian Patent Application No. 2,561,829.
Canadian Notice of Allowance, dated Apr. 14, 2009, for Canadian Patent Application No. 2,561,829.
Chinese Office Action, dated Apr. 28, 2010, for Chinese Patent Application No. 200580011565.9, with English translation.
Chinese Office Action, dated Dec. 23, 2010, for Chinese Patent Application No. 200580011565.9, with English translation.
Chinese Office Action, dated Jun. 9, 2011, for Chinese Patent Application No. 201010246226.1, with English translation.
Chinese Office Action, dated May 6, 2010, for Chinese Patent Application No. 200910138575.9, with English translation.
Chinese Office Action, dated Nov. 21, 2008, for Chinese Patent Application No. 200580011565.9, with English translation.
Chinese Office Action, dated Oct. 19, 2011, for Chinese Patent Application No. 200910138575.9, with English translation.
Chinese Response to Office Action, filed Aug. 4, 2010, for Chinese Patent Application No. 200910138575.9, with English translation.
Chinese Response to Office Action, filed Feb. 21, 2011, for Chinese Patent Application No. 200580011565.9, with English translation.
Chinese Response to Office Action, filed Jul. 12, 2010, for Chinese Patent Application No. 200580011565.9, with English translation.
Chinese Response to Office Action, filed May 7, 2009, for Chinese Patent Application No. 200580011565.9, with English translation.
Chinese Response to Office Action, filed Nov. 16, 2011, for Chinese Patent Application No. 200910138575.9, with English translation.
Chinese Response to Office Action, filed Sep. 20, 2011, for Chinese Patent Application No. 201010246226.1, with English translation.
Egyptian Office Action, dated Dec. 14, 2010, for Egyptian Patent Application No. 1270/2006, with English translation.
Egyptian Office Action, dated Dec. 15, 2009, for Egyptian Patent Application No. 1270/2006, with English translation.
Egyptian Office Action, dated Jul. 30, 2007, for Egyptian Patent Application No. 1270/2006, with English translation.
Egyptian Response to Office Action, filed Mar. 3, 2010, for Egyptian Patent Application No. 1270/2006, with English translation.
Egyptian Response to Office Action, filed on Aug. 25, 2007, for Egyptian Patent Application No. 1270/2006, with English translation.
Filipino Notice of Allowability, dated Feb. 26, 2010, for Filipino Patent Application No. 1-2006-501797.
Filipino Office Action, dated Dec. 17, 2009, for Filipino Patent Application No. 1-2006-501797.
Filipino Response to Office Action, dated Jan. 21, 2010, for Filipino Patent Application No. 1-2006-501797.
Indian Examination Report, dated Nov. 13, 2009, for Indian Patent Application No. 533/CHENP/2007.

(56) References Cited

OTHER PUBLICATIONS

Indian First Examination Report, dated Dec. 15, 2008, for Indian Patent Application No. 533/CHENP/2007.
Indian Response to Examination Report, filed Dec. 8, 2009, for Indian Patent Application No. 533/CHENP/2007.
Indian Response to First Examination Report, filed Apr. 13, 2009, for Indian Patent Application No. 533/CHENP/2007.
International Preliminary Report on Patentability and Written Opinion of the International Searching Authority, dated Jan. 16, 2007, for International Patent Application No. PCT/JP2005/012388.
International Search Report, dated Sep. 20, 2005, for International Patent Application No. PCT/JP2005/012388.
Israeli Notice Prior to Allowance, dated Jul. 27, 2011, for Israeli Patent Application No. 180024, with English translation.
Israeli Notice Prior to Examination, dated Mar. 3, 2009, for Israeli Patent Application No. 180024, with English translation.
Israeli Office Action, dated Jul. 12, 2010, for Israeli Patent Application No. 180024, with English translation.
Israeli Response to Notice Prior to Examination, filed Jun. 25, 2009, for Israeli Patent Application No. 180024, with English translation.
Israeli Response to Office Action, filed Sep. 6, 2010, for Israeli Patent Application No. 180024, with English translation.
Japanese Office Action, dated May 8, 2007, for Japanese Application No. 2006-528904, with English translation.
Japanese Office Action, dated Nov. 21, 2006, for Japanese Application No. 2006-528904, with English translation.
Japanese Written Amendment, filed Jan. 18, 2007, for Japanese Application No. 2006-528904, with English translation.
Japanese Written Amendment, filed Oct. 23, 2006, for Japanese Patent Application No. 2006-528904, with English translation.
Japanese Written Argument, filed Jan. 18, 2007, for Japanese Application No. 2006-528904, with English translation.
Japanese Written Statement, filed Nov. 2, 2006, for Japanese Application No. 2006-528904, with English translation.
Japanese Written Statement, filed Oct. 23, 2006, for Japanese Application No. 2006-528904, with English translation.
Korean Amendment, filed Jun. 2, 2009, for Korean Patent Application No. 10-2006-7020395, with English translation.
Korean Amendment, filed Oct. 11, 2006, for Korean Patent Application No. 10-2006-7020395, with English translation.
Korean Argument Brief, filed Jun. 2, 2009, for Korean Patent Application No. 10-2006-7020395, with English translation.
Korean Notice of Decision for Patent, dated Oct. 29, 2009, for Korean Patent Application No. 10-2006-7020395, with English translation.
Korean Office Action, dated Sep. 3, 2007, for Korean Patent Application No. 10-2006-7020395, with English translation.
Malaysian Amendment, filed Dec. 21, 2009, for Malaysian Patent Application No. PI20052537.
New Zealand Examination Report and Notice of Acceptance, dated Oct. 7, 2009, for New Zealand Patent Application No. 550720.
New Zealand Examination Report, dated Apr. 30, 2009, for New Zealand Patent Application No. 550720.
New Zealand Examination Report, dated Sep. 9, 2009, for New Zealand Patent Application No. 550720.
New Zealand Response to Examination Report, filed Aug. 24, 2009, for New Zealand Patent Application No. 550720.
New Zealand Response to Examination Report, filed Sep. 15, 2009, for New Zealand Patent Application No. 550720.
Pakistani Notice of Acceptance, dated Nov. 5, 2010, for Pakistani Patent Application No. 618/2005.
Pakistani Office Action, dated Jun. 18, 2007, for Pakistani Patent Application No. 618/2005.
Pakistani Response to Office Action, filed Oct. 14, 2010, for Pakistani Patent Application No. 618/2005.
Russian Decision on Grant, dated Oct. 30, 2007, for Russian Patent Application No. 2007104342, with English translation.
Saudi Arabian Appeal before Committee, filed Jan. 26, 2010, for Saudi Arabian Patent Application No. 5260199, with English translation.
Saudi Arabian Examination Report, dated Aug. 26, 2009, for Saudi Arabian Patent Application No. 5260199, with English translation.
Saudi Arabian Examination Report, dated Dec. 7, 2009, for Saudi Arabian Patent Application No. 5260199, with English translation.
Saudi Arabian Examination Report, dated May 13, 2009, for Saudi Arabian Patent Application No. 5260199, with English translation.
Saudi Arabian Rejection from Committee, dated May 16, 2010, for Saudi Arabian Patent Application No. 5260199, with English translation.
Saudi Arabian Response to Examination Report, dated Jul. 27, 2009, for Saudi Arabian Patent Application No. 5260199, with English translation.
Saudi Arabian Response to Examination Report, dated Nov. 14, 2009, for Saudi Arabian Patent Application No. 5260199, with English translation.
South African Amendment, filed Jan. 11, 2007, for South African Patent Application No. 2006/09274.
South African Notice of Acceptance, dated Apr. 24, 2008, for South African Patent Application No. 2006/09274.
Taiwanese Amendment, filed May 18, 2011, for Taiwanese Patent Application No. 094122578, with English translation.
Taiwanese Notice of Allowance, dated Jun. 2, 2011, for Taiwanese Patent Application No. 094122578, with English translation.
Taiwanese Office Action, dated Feb. 21, 2011, for Taiwanese Patent Application No. 094122578, with English translation.
Taiwanese Response, filed May 18, 2011, for Taiwanese Patent Application No. 094122578, with English translation.
Thai Amendment, filed Feb. 23, 2011, for Thai Patent Application No. 0501003082, with English translation.
Vietnamese Response to Office Action, filed Jul. 10, 2008, for Vietnamese Patent Application No. 1-2007-00266, with English translation.
Vietnamese Office Action, dated Jun. 5, 2008, for Vietnamese Patent Application No. 1-2007-00266, wtih English translation.
Extended European Search Report dated Apr. 25, 2012 issued in counterpart European patent application No. 05758232.2.
Notification to Complete Registration Formalities and Notification to Grant Patent Right for Invention dated Apr. 5, 2012 for Chinese Application No. 201010246226.1 with English translation.
Brazilian Office Action for Brazilian Application No. PI0510254-5 dated Jun. 5, 2012 with English translation.
Partial European Search Report dated Mar. 5, 2013 for European Application No. 13152837.4.
European Notice of Allowance dated Nov. 9, 2012 for European Application No. 05758232.2.
Vietnamese Response dated Oct. 5, 2012 to Vietnamese Official Notice for Vietnamese Application No. 1-2007-00266 with English translation.
European Notice of Allowance dated Jan. 7, 2013, for European Application No. 05758232.2.
Brazilian Office Action for Brazilian Application No. PI0111596-0 dated Apr. 17, 2013 with English translation.
Amendment filed on Sep. 6, 2013 for Counterpart Japanese Patent Application No. 2011-224926.
Argument filed on Sep. 6, 2012 for Counterpart Japanese Patent Application No. 2011-224926.
Office Action dated Jul. 9, 2013 issued in Counterpart Japanese Patent Application No. P2011-224926.
Chinese Office Action dated Jun. 4, 2013 issued in counterpart Chinese Patent Application No. 201110261753.4.
Malaysian Notice of Allowance dated Jun. 7, 2013 issued in counterpart Malaysian Patent Application No. PI20052537.
Extended European Search Report dated Jul. 3, 2013 issued in counterpart EP Patent Application No. 13152837.4.
Submission Document(s) Before the Patent Office dated May 17, 2013 in Brazilian Patent Application No. PI0111596-0.
Japanese Office Action, dated Oct. 1, 2013, for counterpart Japanese Application No. P2011-224926 (with English translation).
Amendment filed on Oct. 17, 2013 in Counterpart Japanese Patent Application No. 2011-224926.
Argument filed on Oct. 17, 2013 in Counterpart Japanese Patent Application No. 2011-224926.

(56) References Cited

OTHER PUBLICATIONS

Submission of Document(s) Before the Patent Office dated Sep. 27, 2013 in counterpart CN Patent Application No. 201110261753.4.
Notice of Decision to Grant a Patent dated Nov. 5, 2013 in counterpart Japanese Patent Application No. P2011-224926.
Australian Examination Report issued in Australian Application No. 2005258378 on Jul. 26, 2010.
Australian Response, dated Mar. 29, 2011, to Australian Office Action issued in Australian Application No. 2005258378 on Jul. 26, 2010.
Canadian Office Action issued in Canadian Application No. 2,570,177 on Feb. 3, 2011.
Canadian Office Action issued in Canadian Application No. 2,570,177 on Jun. 9, 2011.
Canadian Response to Canadian Office Action issued in Canadian Application No. 2,570,177 on Feb. 3, 2011.
Canadian Response, dated Jul. 6, 2011, to Canadian Office Action issued in Canadian Application No. 2,570,177 on Jun. 9, 2011.
Chinese Office Action issued in Chinese Application No. 200580023071.2 on Aug. 7, 2009, with English translation.
Chinese Office Action issued in Chinese Application No. 200580023071.2 on Dec. 6, 2010, with English translation.
Chinese Office Action issued in Chinese Application No. 200580023071.2 on Feb. 27, 2009, with English translation.
Chinese Office Action issued in Chinese Application No. 200580023071.2 on May 11, 2010.
Chinese Office Action issued in Chinese Application No. 200580023071.2 on Nov. 20, 2009.
Chinese Rejection Decision issued in Chinese Application No. 200580023071.2 on May 25, 2011, with English translation.
Chinese Request for Re-examination of Chinese Office Action issued in Chinese Application No. 200580023071.2 on May 25, 2011, with English translation.
Chinese Response to Chinese Office Action issued in Chinese Application No. 200580023071.2 on Aug. 7, 2009, with English translation.
Chinese Response to Chinese Office Action issued in Chinese Application No. 200580023071.2 on Dec. 6, 2010, with English translation.
Chinese Response to Chinese Office Action issued in Chinese Application No. 200580023071.2 on Feb. 27, 2009, with English translation.
Chinese Response to Chinese Office Action issued in Chinese Application No. 200580023071.2 on May 11, 2010, with English translation.
Chinese Response to Chinese Office Action issued in Chinese Application No. 200580023071.2 on Nov. 12, 2009, with English translation.
Chinese Supplemental Response with Experimental Data to Chinese Office Action issued in Chinese Application No. 200580023071.2 on May 11, 2010, with English translation.
English translation of Applicant Response to Israeli Office Action issued in Israeli Application No. 180151 on Oct. 24, 2010.
European Examination Report issued in European Application No. 05758231.4 on Aug. 11, 2009.
European Response, dated Dec. 21, 2009, to European Office Action issued in European Application No. 05 758 231.4 on Aug. 11, 2009.
European Supplemental Response, dated Oct. 27, 2010, to European Office Action issued in European Application No. 05 758 231.4 on Aug. 11, 2009.

Extended European Search Report issued in European Application No. 05758231.4 on May 12, 2009.
Indian Notice of Hearing issued in Indian Application No. 7715/DELNO/2006 on Sep. 5, 2011.
Indian Office Action issued in Indian Application No. 7715/DELNP/2006 on Dec. 14, 2009 (stamped Dec. 15, 2009).
Indian Office Action issued in Indian Application No. 7716/DELNP/2006 on Sep. 8, 2010.
Indian Response to Indian Notice of Hearing issued in Indian Application No. 7715/DELNP/2006 on Sep. 5, 2011.
Indian Response to Indian Office Action issued in Indian Application No. 7715/DELNP/2006 on Aug. 8, 2010.
Indian Response to Indian Office Action issued in Indian Application No. 7715/DELNP/2006 on Dec. 15, 2009.
Israeli Office Action, dated Oct. 24, 2010, issued in Israeli Application No. 180151 and Applicant Response, dated Jan. 25, 2011, with English translations.
Japanese Amendment, dated Apr. 17, 2012, for Japanese Application No. 2006-528897, with English translation.
Japanese Amendment, dated May 30, 2012, for Japanese Application No. 2006-528897, with English translation.
Japanese Argument, dated Apr. 17, 2012, for Japanese Application No. 2006-528897, with English translation.
Japanese Certificate of Experiment Results, dated Apr. 16, 2012, for Japanese Application No. 2006-528897, with English translation.
Japanese Decision of Appeal, dated Jun. 22, 2012, for Japanese Application No. 2006-528897, with English translation.
Japanese Decision of Rejection, dated Sep. 17, 2010, for Japanese Application No. 2006-568897.
Japanese Demand for Appeal, dated Dec. 16, 2010, of Decision of Rejection, dated Sep. 13, 2010, for Japanese Application No. 2006-528897, with English translation.
Japanese Notification of Reason for Rejection, dated Feb. 17, 2012, for Japanese Application No. 2006-528897 (Appeal No. 2010-28433), with English translation.
Japanese Notification of Reason for Rejection, dated May 29, 2012, for Japanese Application No. 2006-528897, with English translation.
Japanese Re-Corrected Comparative Experiment Report, dated Apr. 16, 2012, for Japanese Application No. 2006-528897, with English translation.
Japanese Response, dated Jul. 30, 2010, to Japanese Office Action issued in Japanese Application No. 2006-528897 on Jun. 2, 2010 (mailed Jun. 11, 2010), with English translation.
Korean Argument and Amended Claims, dated Mar. 27, 2012, for Korean Application No. 10-2006-7027447, with English translation.
Korean Notice of Allowance, dated Jul. 31, 2012, for Korean Application No. 10-2006-7027447, with English translation.
Korean Notice to Submit a Response, dated Jan. 27, 2012, for Korean Application No. 10-2006-7027447, with English translation.
Korean Office Action, dated May 11, 2011, for Korean Application No. 10-2006-7027447, with English translation.
Korean Response, dated Jul. 11, 2011, to Korean Office Action issued in Korean Application No. 5-2006-031192-0 on May 11, 2011, with English translation.
Notice of Grant issued Feb. 24, 2014 for corresponding Chinese application No. 201110261753.4 with English translation.
Vietnamese Notice of Allowance (including English translation thereof), dated Apr. 28, 2014, issued in Vietnamese Patent Application No. 1-2007-00266.
Certificate of Preliminary Acceptance dated May 6, 2014 issued in JO Patent Application No. 97/2005, with partial English language translation.

* cited by examiner

METHOD FOR PRODUCING 1, 2-DIHYDROPYRIDINE-2-ONE COMPOUND

CROSS-REFERENCES TO RELATED APPLICATIONS

This application is a divisional application of U.S. application Ser. No. 11/649,299 filed on Jan. 4, 2007, which is a continuation-in-part-application of PCT/JP2005/012364, which was internationally filed on Jul. 5, 2005, and claims a priority under the Paris Convention based on JP 2004-198709 filed in Japan on Jul. 6, 2004, and PCT/JP2005/012388, which was internationally filed on Jul. 5, 2005, and claims a priority under the Paris Convention based on JP 2004-198709 filed in Japan on Jul. 6, 2004. All of the contents of Ser. No. 11/649,299, PCT/JP2005/012364, PCT/JP2005/012388 and JP 2004-198709 are hereby expressly incorporated by reference.

BACKGROUND OF THE INVENTION

1. Field of the Invention

The present invention relates to a method for producing a 1,2-dihydropyridine-2-one compound represented by formula (III) which comprises reacting a compound represented by formula (I) with a boronic acid derivative represented by formula (II) in the presence of a palladium compound, a copper compound, a phosphorus compound and a base. Further, the present invention relates to crystals of 3-(2-cyanophenyl)-5-(2-pyridyl)-1-phenyl-1,2-dihydropyridine-2-one and a method for producing the crystals.

The compound of formula (III) represented by 3-(2-cyanophenyl)-5-(2-pyridyl)-1-phenyl-1,2-dihydropyridine-2-one is useful as, for example, a therapeutic agent for diseases such as Parkinson's disease, multiple sclerosis, epilepsy, etc.

2. Description of the Related Art

Background art concerning a method for producing the compound of formula (III) is explained below.

In the production method 2 in WO 01/96308, the coupling reaction of a compound (viii) with an arylboronic acid derivative by the use of a palladium catalyst is described as to a final step for producing a compound (I-1), but the reaction in the presence of a palladium compound, a copper compound and a phosphorus compound is neither suggested nor described which is characteristic of the present invention.

Production Method 2

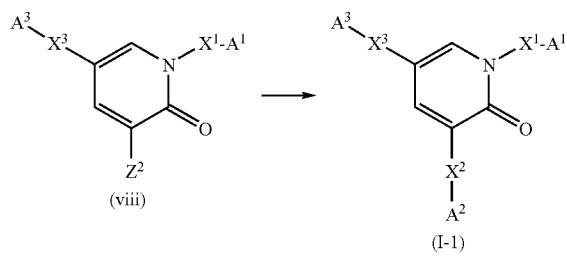

(viii)    (I-1)

Also in the production method 3 in WO 01/96308, the coupling reaction of a compound WO with an arylboronic acid derivative by the use of a palladium catalyst is described as to a final step for producing a compound (I-1), but the reaction in the presence of a palladium compound, a copper compound and a phosphorus compound is neither suggested nor described which is characteristic of the present invention.

Production Method 3

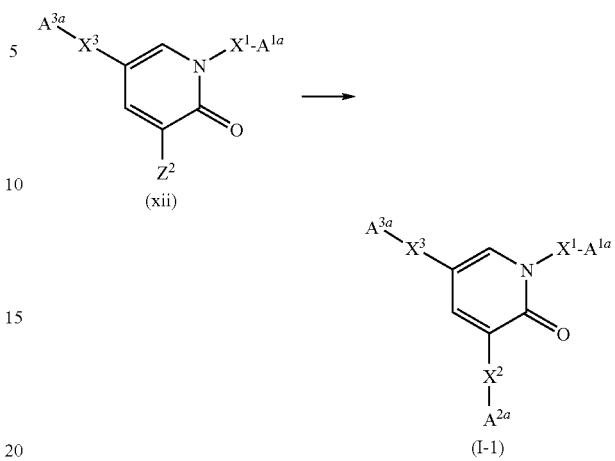

(xii)

(I-1)

The compound of formula (III-a) described hereinafter is a well-known compound. In Example 7 in WO 01/96308, it is known that as shown in the following reaction scheme, this compound may be produced by reacting 3-(2-cyanophenyl)-5-(2-pyridyl)-2(1H)-pyridone with phenylboronic acid in the presence of copper acetate and triethylamine. But, there is neither suggested nor described a method for producing a compound of formula (III) by the reaction of a compound of formula (I) with a compound of formula (II) in the presence of a palladium compound, a copper compound, a phosphorus compound and a base which is characteristic of the present invention.

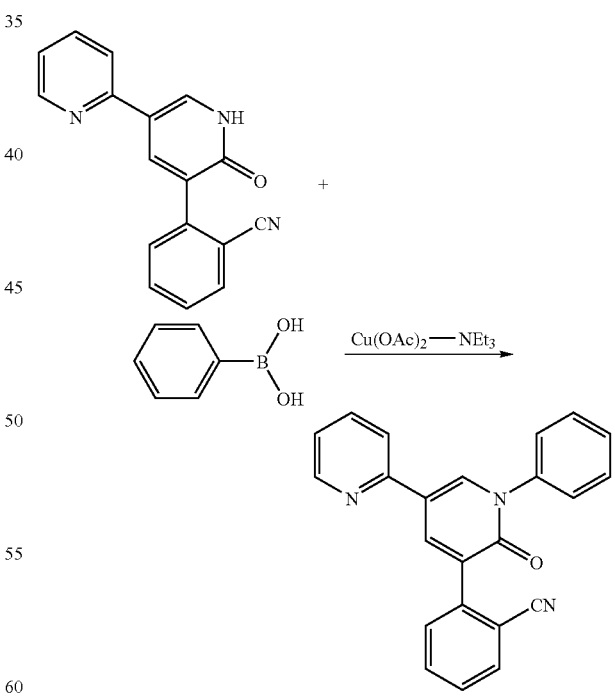

As to the compound of formula (I) represented by 3-bromo-5-(2-pyridyl)-1-phenyl-1,2-dihydropyridine-2-one (III-a), a method for producing this compound is described in claim 49 and Example 404 in WO 01/96308.

On the other hand, the effect of a copper catalyst in the Suzuki reaction is described in G. M. Boland et al., J. Chem.

Soc., Perkin Trans. 1, 2591-2587(1996). Although this reference describes "Pd(PPh$_3$)$_4$-CuI", copper iodide is used in a large amount of 1.1 equivalents per equivalent of a starting material in the reference. The reference neither suggests nor describes the progress of the reaction in the presence of a palladium compound, a copper compound and a phosphorus compound, in particular, the reaction in the presence of a catalytic amount of the copper compound, which is characteristic of the present invention.

On the other hand, among the compounds of formula (III), particularly, 3-(2-cyanophenyl)-5-(2-pyridyl)-1-phenyl-1,2-dihydropyridin-2-one (hereafter referred to as Compound (A) in some cases) shows significant antagonistic action against AMPA (alpha-amino-3-hydroxy-5-methyl-4-isoxazolepropionic acid) receptor (see WO 01/96308).

Although Example 7 in WO 01/96308 discloses a process for producing the compound (A), there is merely described, "the residue is purified by silica gel column chromatography (ethyl acetate/hexane=1:2)" and there is no disclosure of the form of the obtained compound.

SUMMARY OF THE INVENTION

When in each of the methods using a palladium catalyst described as the production method 2 and production method 3 in WO 01/96308, the reaction is carried out in the presence of, for example, "palladium acetate catalyst-cesium carbonate-water", there are various problems such as the following problems: a considerable amount of compounds are produced as by-products by the cleavage of the carbon-boron bond of a compound (II) (Yoshio Urawa and three others, Pharmacia, 35(7), 706-710(1999)) and the hydrolysis of a substituent such as a nitrile group proceeds. Therefore, an industrial method for producing a compound represented by formula (III) is desired.

Accordingly, an object of the present invention is to provide a method for industrially producing a compound of formula (III) having an excellent therapeutic effect on diseases such as Parkinson's disease, multiple sclerosis, epilepsy, etc., in good yield and high purity.

On the other hand, when a compound existing in crystal polymorphism is used as a medicament, it is necessary to stably supply the compound having uniform crystal form so that the uniform quality and the consistent potency required for the medicament may be guaranteed. There is also a need for the crystal form capable of maintaining the same quality during its storage and its formulation process such as blending and granulation.

Since a drug substance is industrially used in a large amount, desirable crystal forms are those having high explosion concentration high limit and minimum ignition energy, index of explosiveness and dangerousness.

Generally, powders that tend to be charged have great adhesiveness to other objects; and there is concern about their adhesion to protective goods or the skin.

When a drug substance has chargeability, it happens that the production efficiency and workability lower if the compound adheres to a rotary blade at a milling stage in the manufacture of the compound, or adheres to and agglomerate on the production machines during the process of formulation. When a large quantity of powders having chargeability is processed on an industrial scale, there is the possibility that dust explosion will occur. It is, therefore, desired that a compound crystal having weak chargeability be used as the drug substance.

As for a compound having high pharmacological activity such as the drug substance, the standpoint of the avoidance of exposure to the workers and the prevention of the facility contamination makes powders that do not tend to be charged desirable.

For the reasons above, when the active pharmaceutical ingredient of a medicament is obtained as a crystalline substance, it desirably comprises a homogeneous crystal form, has consistently preferable properties, and does not contain impurities such as metals. There has also been a need to develop a process for stably producing such crystals on an industrial scale.

Accordingly, an object of the present invention to provide a crystal comprising a homogeneous crystal form of Compound (A) and a production process therefor.

The present inventors earnestly investigated in order to solve the above problems, and consequently found the following production method of the compound of formula (III), crystal form of Compound (A) and production method of the crystal form, whereby the present invention has been accomplished. That is, the present invention relates to the following production methods 1) to 13), crystal forms 14) to 19), production methods 20) to 28), crystal forms 29) to 38), medicament 39), composition 40) and agents 41) to 50).

1) A method for producing a compound represented by formula (III):

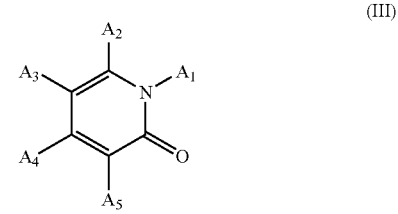

wherein $A_1$, $A_2$, $A_3$, $A_4$ and $A_5$ are as defined below, or a salt thereof, which comprises reacting a compound represented by formula (I):

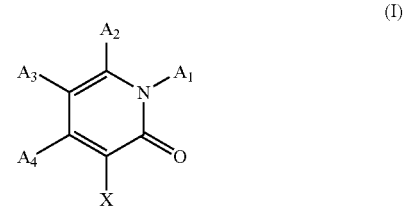

wherein each of $A_1$, $A_2$, $A_3$ and $A_4$, which may be the same or different, is a hydrogen atom, an optionally substituted 6- to 14-membered aromatic hydrocarbon ring group or an optionally substituted 5- to 14-membered heteroaromatic ring group, and X is a leaving group, or a salt thereof with a compound represented by formula (II):

wherein $A_5$ is an optionally substituted 6- to 14-membered aromatic hydrocarbon ring group or an optionally substituted 5- to 14-membered heteroaromatic ring group; and R1 and R2 are as follows: 1) each of R1 and R2, which may be the same or different, is a hydrogen atom or a C1-6 alkyl group, and 2) the compound of formula (II) may form boroxine (a trimer) when both R1 and R2 are hydrogen atoms, or 3) R1, R2, the oxygen atoms and the boron atom, when taken together, form a 5- or 6-membered ring group optionally substituted by one to four C1-6 alkyl groups, in the presence of a palladium compound, a copper compound, a phosphorus compound and a base.

2) A production method according to 1) above, wherein each of $A_2$ and $A_4$ is a hydrogen atom.

3) A production method according to 1) or 2) above, wherein each of $A_1$, $A_3$ and $A_5$ is a phenyl group, a pyridyl group, a pyrimidyl group, a thienyl group or a furyl group.

4) A production method according to any one of 1) to 3) above, wherein a compound represented by formula (III-a):

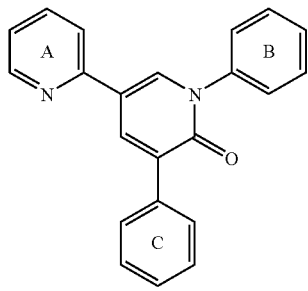

(III-a)

wherein the ring A, ring B and ring C are as defined below, or a salt thereof is produced by reacting a compound represented by formula (I-a):

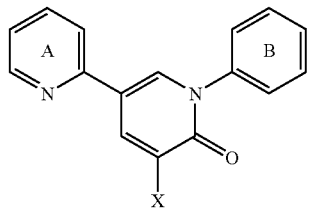

(I-a)

wherein the ring A is an optionally substituted 2-pyridyl group, the ring B is an optionally substituted phenyl group, and X is a leaving group, or a salt thereof with a compound represented by formula (II-a):

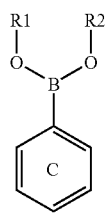

(II-a)

wherein the ring C is an optionally substituted phenyl group; and R1 and R2 are as follows: 1) each of R1 and R2, which may be the same or different, is a hydrogen atom or a C1-6 alkyl group, and 2) the compound of formula (II-a) may form boroxine (a trimer) when both R1 and R2 are hydrogen atoms, or 3) R1, R2, the oxygen atoms and the boron atom, when taken together, form a 5- or 6-membered ring group optionally substituted by one to four C1-6 alkyl groups, in the presence of a palladium compound, a copper compound, a phosphorus compound and a base.

5) A production method according to 4) above, wherein a compound represented by formula (III-b):

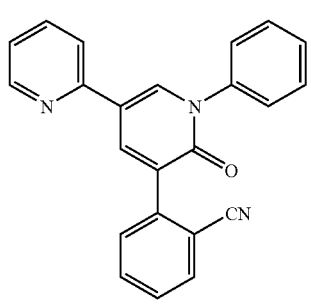

(III-b)

or a salt thereof is produced by reacting a compound represented by formula (I-b):

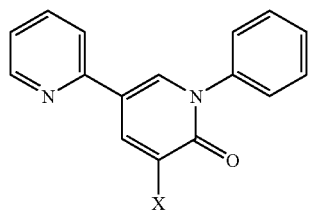

(I-b)

wherein X is a leaving group, or a salt thereof with a compound represented by formula (II-b):

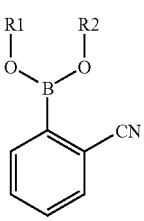

(II-b)

wherein R1 and R2 are as defined above, in a solvent in the presence of a palladium compound, a copper compound, a phosphorus compound and a base.

6) A production method according to 5) above, wherein the compound (II-b) is a compound represented by formula (II-b-1), formula (II-b-2), formula (II-b-3) or formula (II-b-4):

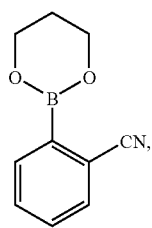
(II-b-1)

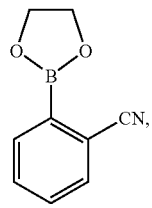
(II-b-2)

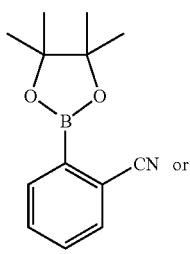
(II-b-3)

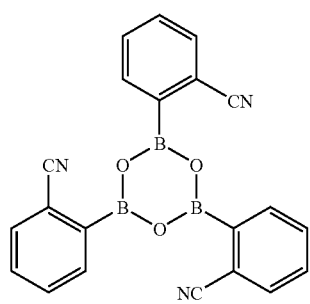
(II-b-4)

7) A production method according to any one of 1) to 6) above, wherein X is a halogen atom, an alkylsulfonyloxy group or an arylsulfonyloxy group.

8) A production method according to any one of 1) to 7) above, wherein the palladium compound is palladium acetate, palladium chloride or palladium hydroxide.

9) A production method according to any one of 1) to 8) above, wherein the phosphorus compound is triphenylphosphine or tri-tert-butylphosphine.

10) A production method according to any one of 1) to 9) above, wherein the copper compound is cuprous bromide, cuprous iodide, cuprous chloride or cuprous acetate.

11) A production method according to any one of 1) to 10) above, wherein the base is cesium carbonate, sodium carbonate or potassium carbonate.

12) A production method according to any one of 1) to 11) above, wherein the copper compound is used in an amount of 0.01 to 0.05 mole per mole of the compound represented by formula (I).

13) A production method according to any one of 1) to 12) above, wherein the reaction is carried out in a solvent and 1,2-dimethoxyethane or toluene is used as the solvent for reaction.

14) A crystal of 3-(2-cyanophenyl)-5-(2-pyridyl)-1-phenyl-1,2-dihydropyridin-2-one hydrate having a diffraction peak at a diffraction angle (2θ±0.2°) of 8.7° in a powder X-ray diffraction (Hydrate crystal).

15) A crystal of 3-(2-cyanophenyl)-5-(2-pyridyl)-1-phenyl-1,2-dihydropyridin-2-one hydrate having a diffraction peak at a diffraction angle (2θ±0.2°) of 12.5° in a powder X-ray diffraction (Hydrate crystal).

16) A crystal of 3-(2-cyanophenyl)-5-(2-pyridyl)-1-phenyl-1,2-dihydropyridin-2-one hydrate having diffraction peaks at diffraction angles (2θ±0.2°) of 8.7° and 12.5° in a powder X-ray diffraction (Hydrate crystal).

17) A crystal of 3-(2-cyanophenyl)-5-(2-pyridyl)-1-phenyl-1,2-dihydropyridin-2-one hydrate having an absorption peak at a wavenumber of 1588±1 cm$^{-1}$ in an infrared absorption spectrum (KBr method) (Hydrate crystal).

18) A crystal of 3-(2-cyanophenyl)-5-(2-pyridyl)-1-phenyl-1,2-dihydropyridin-2-one hydrate having absorption peaks at wavenumbers of 1588±1 cm$^{-1}$ and 751±1 cm$^{-1}$ in an infrared absorption spectrum (KBr method) (Hydrate crystal).

18-2) The crystal according to any one of 14) to 16) above having an absorption peak at a wavenumber of 1588±1 cm$^{-1}$ in an infrared absorption spectrum (KBr method) (Hydrate crystal).

18-3) The crystal according to any one of 14) to 16) above having absorption peaks at wavenumbers of 1588±1 cm$^{-1}$ and 751±1 cm$^{-1}$ in an infrared absorption spectrum (KBr method) (Hydrate crystal).

18-4) The crystal according to any one of 14) to 18), 18-2) and 18-3) above having a palladium content of 20 ppm or less, preferably 15 ppm or less (Hydrate crystal).

19) A crystal of 3-(2-cyanophenyl)-5-(2-pyridyl)-1-phenyl-1,2-dihydropyridin-2-one hydrate having peaks at chemical shifts of around 146.7 ppm and around 123.3 ppm in a $^{13}$C Solid State Nuclear Magnetic Resonance spectrum (Hydrate crystal).

20) A process for producing a crystal of 3-(2-cyanophenyl)-5-(2-pyridyl)-1-phenyl-1,2-dihydropyridin-2-one hydrate according to any one of 14) to 18), 18-1), 18-2), 18-3), 18-4) and 19) above, the process comprising the step of crystallizing 3-(2-cyanophenyl)-5-(2-pyridyl)-1-phenyl-1,2-dihydropyridin-2-one with an aid of one or two crystallization solvents selected from the group consisting of an alcoholic solvent, an alkylketone solvent, and water.

21) The process according to 20) above, wherein the crystallization solvent is a mixed solvent of acetone and water.

22) The process according to 20) above, wherein the crystallization solvent is a mixed solvent of acetone and water with a volume ratio of 37:3 to 24:16, preferably a mixed solvent of acetone and water with a volume ratio of 9:1 to 7:3, and more preferably a mixed solvent of acetone and water with a volume ratio of 8:2 formed by dissolving the crystals in a mixed solvent of acetone and water with a volume ratio of 9:1 and thereafter adding water to the mixed solvent.

23) The process according to any one of 20) to 22) above, wherein the crystallization is carried out at a temperature of 60 to −30° C.

24) The process according to any one of 20) to 22) above comprising the steps of heating a solution of 3-(2-cyanophenyl)-5-(2-pyridyl)-1-phenyl-1,2-dihydropyridin-2-one dissolved in the crystallization solvent at a temperature of 50° C. or more (preferably at a temperature of the reflux temperature of the crystallization solvent to 50° C., more preferably at a temperature of 65 to 55° C.) and thereafter cooling the solution to a temperature of 10 to −20° C.

(preferably to a temperature of 10 to 5° C.) at a cooling rate of 40 to 5° C. per hour (preferably at a cooling rate of 25 to 15° C. per hour).

25) The process according to any one of 20) to 24) above, wherein the crystallization solvent is used in a volume ratio of 10- to 50-fold (v/w) based on the weight of 3-(2-cyanophenyl)-5-(2-pyridyl)-1-phenyl-1,2-dihydropyridin-2-one. The quantity of the crystallization solvent is preferably from 30- to 50-fold (v/w), more preferably about 40-fold (v/w) where acetone and water (9:1) is used as the crystallization solvent and about 45-fold (v/w) where acetone and water (8:2) is used as the crystallization solvent.

26) The process according to any one of 20) to 25) above, wherein seed crystals (a small amount of crystals of 3-(2-cyanophenyl)-5-(2-pyridyl)-1-phenyl-1,2-dihydropyridin-2-one hydrate) are added at a temperature of 60° C. or less (preferably at a temperature of 55 to 0° C., more preferably 55 to 35° C., and most preferably about 40° C.).

27) The process according to any one of 20) to 26) above, wherein the crystals are dried under reduced pressure after the crystallization.

28) The process according to any one of 20) to 27) above, wherein the crystals are allowed to stand in the atmosphere after the crystallization and the drying under reduced pressure.

28-1) The process according to any one of 20) to 26) above, wherein the crystals are allowed to stand in the atmosphere after the crystallization.

28-2) The process according to 27) above, wherein the crystals are allowed to stand in the atmosphere after the drying under reduced pressure.

29) An anhydrous crystal of 3-(2-cyanophenyl)-5-(2-pyridyl)-1-phenyl-1,2-dihydropyridin-2-one having a diffraction peak at a diffraction angle (2θ±0.2°) of 10.3° in a powder X-ray diffraction (Anhydrous crystal form I).

30) The crystal according to 29) above further having a diffraction peak at a diffraction angle (2θ±0.2°) of 19.1° in a powder X-ray diffraction (Anhydrous crystal form I).

31) An anhydrous crystal of 3-(2-cyanophenyl)-5-(2-pyridyl)-1-phenyl-1,2-dihydropyridin-2-one having peaks at chemical shifts of around 149.0 ppm and around 125.6 ppm in a $^{13}$C Solid State Nuclear Magnetic Resonance spectrum (Anhydrous crystal form I).

32) An anhydrous crystal of 3-(2-cyanophenyl)-5-(2-pyridyl)-1-phenyl-1,2-dihydropyridin-2-one having a diffraction peak at a diffraction angle (2θ±0.2°) of 16.7° in a powder X-ray diffraction (Anhydrous crystal form V).

33) The crystal according to 32) above further having diffraction peaks at diffraction angles (2θ±0.2°) of 12.9° and 24.9° in a powder X-ray diffraction (Anhydrous crystal form V).

34) An anhydrous crystal of 3-(2-cyanophenyl)-5-(2-pyridyl)-1-phenyl-1,2-dihydropyridin-2-one having an absorption peak at a wavenumber of 1658±1 cm$^{-1}$ in an infrared absorption spectrum (KBr method) (Anhydrous crystal form V).

35) The crystal according to 34) above further having an absorption peak at a wavenumber of 501±1 cm$^{-1}$ in an infrared absorption spectrum (KBr method) (Anhydrous crystal form V).

36) An anhydrous crystal of 3-(2-cyanophenyl)-5-(2-pyridyl)-1-phenyl-1,2-dihydropyridin-2-one having peaks at chemical shifts of around 145.9 ppm and around 137.7 ppm in a $^{13}$C Solid State Nuclear Magnetic Resonance spectrum (Anhydrous crystal form V).

37) An anhydrous crystal of 3-(2-cyanophenyl)-5-(2-pyridyl)-1-phenyl-1,2-dihydropyridin-2-one having diffraction peaks at diffraction angles (2θ±0.2°) of 23.7° and 25.0° in a powder X-ray diffraction (Anhydrous crystal form III).

38) The crystal according to 32) above further having diffraction peaks at diffraction angles (2θ±0.2°) of 5.7° and 9.5° in a powder X-ray diffraction (Anhydrous crystal form III).

39) A medicament comprising the crystal according to 14) above.

40) A pharmaceutical composition comprising the crystal according to 14) above.

41) A therapeutic or prophylactic agent for an acute neurodegenerative disease comprising the crystal according to 14) above.

42) A therapeutic or prophylactic agent for neuropathy caused by acute phase of cerebrovascular disorder, head injury, spinal cord injury or hypoxia, or neuropathy caused by hypoglycemia, comprising the crystal according to 14) above.

43) A therapeutic or prophylactic agent for a chronic neurodegenerative disease comprising the crystal according to 14) above.

44) A therapeutic or prophylactic agent for Alzheimer's disease, Parkinson's disease, Huntington's chorea, amyotrophic lateral sclerosis or spinocerebellar degeneration, comprising the crystal according to 14) above.

45) A therapeutic or prophylactic agent for epilepsy, hepatic encephalopathy, peripheral neuropathy, Parkinsonism, spastic paralysis, pain, neuralgia, schizophrenia, anxiety, drug-dependence, nausea, vomiting, dysuria, vision impairment caused by glaucoma, hearing impairment caused by antibiotics, or food poisoning, the agent comprising the crystal according to 14) above.

46) A therapeutic or prophylactic agent for infectious encephalomyelitis, cerebrovascular dementia, or dementia or neurological symptom caused by meningitis, comprising the crystal according to 14) above.

47) A therapeutic or prophylactic agent for a demyelinating disease comprising the crystal according to 14) above.

48) The therapeutic or prophylactic agent according to 47) above, wherein the infectious encephalomyelitis is HIV encephalomyelitis.

49) The therapeutic or prophylactic agent according to 47) above, wherein the demyelinating disease is encephalitis, acute sporadic encephalomyelitis, multiple sclerosis, acute polyradiculoneuropathy, Guillain-Barre syndrome, chronic inflammatory demyelinating polyradiculoneuropathy, Marchifava-Bignami disease, central pontomedullary myelinolysis, neuromyelitis optica, Devic's disease, Balo's disease, HIV-associated myelopathy, HTLV-associated myelopathy, progressive multifocal leukoencephalitis or a secondary demyelinating disease.

50) The therapeutic or prophylactic agent according to 49) above, wherein the secondary demyelinating disease is CNS lupus erythematosus, polyarteritis nodosa, Sjoegren's syndrome, sarcoidosis or dissociated cerebral vasculitis.

DESCRIPTION OF THE PREFERRED EMBODIMENTS

Figure 1:
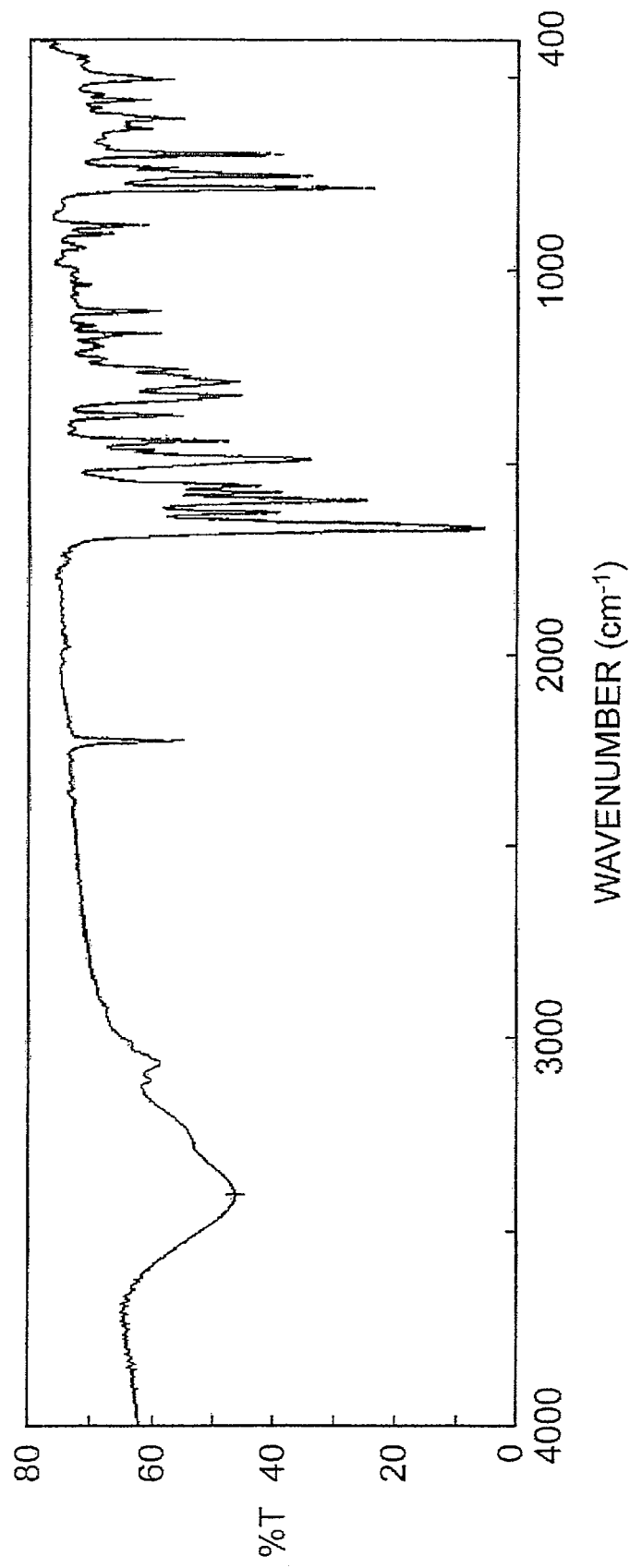
FIG. 1 shows an infrared spectrum (KBr method) of the crystals obtained in Example 5.

The symbols and terms used in the present specification are explained below.

The term "6- to 14-membered aromatic hydrocarbon ring group" means an aromatic hydrocarbon ring group comprising 6 to 14 carbon atoms and also includes fused-ring groups such as monocyclic groups, bicyclic groups, tricyclic groups, etc. Specific examples of said group are phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, etc.

The term "5- to 14-membered heteroaromatic ring group" means a monocyclic, bicyclic or tricyclic 5- to 14-membered heteroaromatic ring group containing one or more heteroatoms selected from the group consisting of nitrogen atom, sulfur atom and oxygen atom. Specific examples of said group are 1) nitrogen-containing heteroaromatic ring groups such as pyrrolyl group, pyridyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolyl group, isoquinolyl group, quinolizinyl group, phthalazyl group, naphthyridinyl group, quinoxalyl group, quinazolinyl group, cinnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenazinyl group, imidazopyridinyl group, imidazopyrimidinyl group, pyrazolopyridinyl group, etc., 2) sulfur-containing heteroaromatic ring groups such as thienyl group, benzothienyl group, etc., 3) oxygen-containing heteroaromatic ring groups such as furyl group, pyranyl group, cyclopentapyranyl group, benzofuryl group, isobenzofuryl group, etc., and 4) heteroaromatic ring groups containing two or more heteroatoms of different kinds, such as thiazolyl group, isothiazolyl group, benzothiazolyl group, benzthiadiazolyl group, phenothiazinyl group, isoxazolyl group, furazanyl group, phenoxazinyl group, oxazolyl group, isoxazolyl group, benzoxazolyl group, oxadiazolyl group, pyrazoloxazolyl group, imidazothiazolyl group, thienofuranyl group, furopyrrolyl group, pyridoxazinyl group, etc.

Each of $A_1$, $A_2$, $A_3$ and $A_4$ is a hydrogen atom, an optionally substituted 6- to 14-membered aromatic hydrocarbon ring group or an optionally substituted 5- to 14-membered heteroaromatic ring group. More preferably, each of $A_2$ and $A_4$ is a hydrogen atom and each of $A_1$ and $A_3$ is an optionally substituted 6- to 14-membered aromatic hydrocarbon ring group or an optionally substituted 5- to 14-membered heteroaromatic ring group. Most preferably, each of $A_1$ and $A_3$ is, for example, an optionally substituted phenyl, pyridyl, pyrimidinyl, thienyl or furyl group.

$A_5$ is an optionally substituted 6- to 14-membered aromatic hydrocarbon ring group or an optionally substituted 5- to 14-membered heteroaromatic ring group. $A_5$ is more preferably, for example, an optionally substituted phenyl, pyrrolyl, pyridyl, pyridazinyl, pyrimidinyl, pyrazinyl, thienyl, thiazolyl, furyl, naphthyl, quinolyl, isoquinolyl, indolyl, benzimidazolyl, benzothiazolyl, benzoxazolyl, imidazopyridyl or pyrrolidinyl group. $A_5$ is most preferably, for example, an optionally substituted phenyl, pyridyl, pyrimidinyl, thienyl or furyl group.

When the group represented by any of $A_1$, $A_2$, $A_3$, $A_4$ and $A_5$ in the above formula is an optionally substituted 6- to 14-membered aromatic hydrocarbon ring group or an optionally substituted 5- to 14-membered heteroaromatic ring group, it may have one to four substituents which may be the same or different and are selected from the following substituents.

In the above formula, the ring A is an optionally substituted 2-pyridyl group and each of the ring B and the ring C is an optionally substituted phenyl group. The ring A, ring B and ring C may also have one to four substituents which may be the same or different and are selected from the following substituents.

The substituents include, for example, hydroxyl group, nitrile groups, halogen atoms, C1-6 alkyl groups, C2-6 alkenyl groups, C2-6 alkynyl groups, C3-8 cycloalkyl groups, C1-6 alkoxy groups, C1-6 alkylthio groups, C1-6 alkoxycarbonyl groups, C1-6 alkanoyl groups (C1-6 alkylcarbonyl groups), C1-6 alkylsulfonyl groups, amino group optionally substituted by a C1-6 alkyl group, amino group optionally substituted by a formyl group, amino group optionally substituted by a C1-6 alkanoyl group, amino group optionally substituted by a C1-6 alkylsulfonyl group, carbamoyl group optionally substituted by one or two C1-6 alkyl groups, and C1-6 alkoxyimino groups. Of these, the nitrile groups and halogen atoms are preferable.

The term "halogen atoms" means a fluorine atom, chlorine atom, bromine atom, iodine atom and the like. The halogen atoms are preferably a chlorine atom and a bromine atom.

The term "C1-6 alkyl groups" means alkyl groups of 1 to 6 carbon atoms. Preferable examples of these groups are linear or branched alkyl groups such as methyl group, ethyl group, n-propyl group, i-propyl group, n-butyl group, i-butyl group, tert-butyl group, n-pentyl group, i-pentyl group, neopentyl group, n-hexyl group, 1-methylpropyl group, 1,2-dimethylpropyl group, 2-ethylpropyl group, 1-methyl-2-ethylpropyl group, 1-ethyl-2-methylpropyl group, 1,1,2-triraethylpropyl group, 1-methylbutyl group, 2-methylbutyl group, 1,1-dimethylbutyl group, 2,2-dimethylbutyl group, 2-ethylbutyl group, 1,3-dimethylbutyl group, 2-methylpentyl group, 3-methylpentyl group, etc.

The term "C2-6 alkenyl groups" means alkenyl groups of 2 to 6 carbon atoms. Preferable examples of these groups are linear or branched alkenyl groups such as vinyl group, allyl group, 1-propenyl group, isopropenyl group, 1-buten-1-yl group, 1-buten-2-yl group, 1-buten-3-yl group, 2-buten-1-yl group, 2-buten-2-yl group, etc.

The term "C2-6 alkynyl groups" means alkynyl groups of 2 to 6 carbon atoms. Preferable examples of these groups are linear or branched alkynyl groups such as ethynyl group, 1-propynyl group, 2-propynyl group, butynyl group, pentynyl group, hexynyl group, etc.

The term "C3-8 cycloalkyl groups" means cyclic alkyl groups of 3 to 8 carbon atoms. Preferable examples of these groups are cyclopropyl group, cyclobutyl group, cyclopentyl group, cyclohexyl group, cycloheptyl group, cyclooctyl group, etc.

The term "C1-6 alkoxy groups" means groups formed by the replacement of a hydrogen atom of an alkyl group of 1 to 6 carbon atoms by an oxygen atom. Preferable examples of said groups are methoxy group, ethoxy group, n-propoxy group, i-propoxy group, sec-propoxy group, n-butoxy group, i-butoxy group, sec-butoxy group, tert-butoxy group, n-pentyloxy group, i-pentyloxy group, sec-pentyloxy group, tert-pentyloxy group, n-hexyloxy group, i-hexyloxy group, 1,2-dimethylpropoxy group, 2-ethylpropoxy group, 1-methyl-2-ethylpropoxy group, 1-ethyl-2-methylpropoxy group, 1,1,2-trimethylpropoxy group, 1,1-dimethylbutoxy group, 2,2-dimethylbutoxy group, 2-ethylbutoxy group, 1,3-dimethylbutoxy group, 2-methylpentyloxy group, 3-methylpentyloxy group, hexyloxy group, etc.

The term "C1-6 alkylthio groups" means groups formed by the replacement of a hydrogen atom of an alkyl group of 1 to 6 carbon atoms by a sulfur atom. Preferable examples of said groups are methylthio group, ethylthio group, n-propylthio group, i-propylthio group, n-butylthio group, i-butylthio group, tert-butylthio group, n-pentylthio group, i-pentylthio group, neopentylthio group, n-hexylthio group, 1-methylpropylthio group, etc.

The term "C1-6 alkoxycarbonyl groups" means groups formed by bonding of a carbonyl group to any of the above-exemplified alkoxy groups. Preferable examples of said groups are methoxycarbonyl group, ethoxycarbonyl group, etc.

The term "C1-6 alkanoyl groups (C1-6 alkylcarbonyl groups)" means groups formed by the replacement of a hydrogen atom of an alkyl group of 1 to 6 carbon atoms by a carbonyl group. Preferable examples of said groups are acetyl group, propionyl group, butyryl group, etc.

The term "C1-6 alkylsulfonyl groups" means groups formed by the replacement of a hydrogen atom of an alkyl group of 1 to 6 carbon atoms by a sulfonyl group. Preferable examples of said groups are methanesulfonyl group, ethanesulfonyl group, etc.

The term "amino group optionally substituted by a C1-6 alkyl group" means an amino group that may have an alkyl group of 1 to 6 carbon atoms bonded thereto. Preferable examples of such an amino group are amino group, methylamino group, ethylamino group, propylamino group, etc.

"Amino group optionally substituted by a formyl group" includes, for example, amino group, formylamino group, etc.

The term "amino group optionally substituted by a C1-6 alkanoyl group" means an amino group that may have an alkanoyl group of 1 to 6 carbon atoms bonded thereto. Preferable examples of such an amino group are acetylamino group, propionylamino group, butyrylamino group, etc.

The term "amino group optionally substituted by a C1-6 alkylsulfonyl group" means an amino group that may have an alkylsulfonyl group of 1 to 6 carbon atoms bonded thereto. Preferable examples of such an amino group are amino group, methanesulfonylamino group, ethanesulfonylamino group, n-propanesulfonylamino group, n-butanesulfonylamino group, N-methylmethanesulfonylamino group, etc.

The term "carbamoyl group optionally substituted by one or two C1-6 alkyl groups" means a carbamoyl group one or two hydrogen atoms of which may be replaced by one or two, respectively, C1-6 alkyl groups. Preferable examples of said groups are N-methylcarbamoyl group, N,N-dimethylcarbamoyl group, N-ethylcarbamoyl group, N,N-diethylcarbamoyl group, etc.

The term "C1-6 alkoxyimino groups" means groups formed by the replacement of a hydrogen atom of an imino group by a C1-6 alkoxy group. Preferable examples of said groups are methoxyimino group, ethoxyimino group, etc.

The passage "X is a leaving group" means that X is a halogen atom, an alkylsulfonyloxy group or an arylsulfonyloxy group.

The passage "X is a halogen atom, an alkylsulfonyloxy group or an arylsulfonyloxy group" means that X is a halogen atom such as fluorine atom, chlorine atom, bromine atom or iodine atom; an alkylsulfonyloxy group such as trifluoromethanesulfonyloxy group; or an arylsulfonyloxy group such as phenylsulfonyloxy group. X is preferably a halogen atom such as chlorine atom or bromine atom, or an alkylsulfonyloxy group such as trifluoromethanesulfonyloxy group.

The sentence "R1 and R2 are as follows: 1) each of R1 and R2, which may be the same or different, is a hydrogen atom or a C1-6 alkyl group, and 2) the compound (II) may form boroxine (a trimer) when both R1 and R2 are hydrogen atoms, or 3) R1, R2, the oxygen atoms and the boron atom, when taken together, form a 5- or 6-membered ring group optionally substituted by one to four C1-6 alkyl groups" in the case of the compound (II) means that the compound (II) is, for example, a phenylboronic acid derivative in which the hydrogen atom of the hydroxyl group may be replaced by a C1-6 alkyl group; a 2-phenyl[1,3,2]-dioxoboronate the ring-forming methylene groups of which may be substituted by one to four C1-6 alkyl groups; or a 2-phenyl-[1,3,2]-dioxoboronate derivative the ring-forming methylene groups of which may be substituted by one to four C1-6 alkyl groups.

In particular, the passage "the compound (II) may form boroxine (a trimer) when both R1 and R2 are hydrogen atoms" means that when both R1 and R2 are hydrogen atoms, the compound (II) may be a monomer or may form a cluster such as a dimer or boroxine (a trimer).

The term "a palladium compound, a copper compound and a phosphorus compound" means a combination of a palladium compound selected from the palladium compounds described hereinafter, a copper compound selected from the copper compounds described hereinafter, and a phosphorus compound selected from the phosphorus compounds described hereinafter.

The compound (I-a) is included in the compound represented by formula (I) and corresponds to a compound of formula (I) in which $A_1$ is an optionally substituted phenyl group, each of $A_2$ and $A_4$ is a hydrogen atom, and $A_3$ is an optionally substituted 2-pyridyl group.

The compound (I-b) is included in the compound represented by formula (I-a) and corresponds to a compound of formula (I-a) in which $A_1$ is a phenyl group, each of $A_2$ and $A_4$ is a hydrogen atom, and $A_3$ is a 2-pyridyl group.

The compound (II-a) is included in the compound represented by formula (II) and corresponds to a compound of formula (II) in which $A_5$ is an optionally substituted phenyl group.

The compound (II-b) is included in the compound represented by formula (II-a) and corresponds to a compound of formula (II-a) in which $A_5$ is a 2-cyanophenyl group.

The compounds (II-b-1), (II-b-2), (II-b-3) and (II-b-4) are included in the compound represented by formula (II-b). Each of the compounds (II-b-1), (II-b-2) and (II-b-3) corresponds to a compound of formula (II-b) in which R1, R2, the oxygen atoms and the boron atom are taken together to form a 5- or 6-membered ring group optionally substituted by one to four C1-6 alkyl groups. The compound (II-b-4) corresponds to boroxine (a timer) formed by a compound of formula (II-b) in which both R1 and R2 are hydrogen atoms.

The compound (III-a) is included in the compound represented by formula (III) and corresponds to a compound of formula (III) in which each of $A_1$ and $A_5$ is an optionally substituted phenyl group, each of $A_2$ and $A_4$ is a hydrogen atom, and $A_3$ is an optionally substituted 2-pyridyl group.

The compound (III-b) is included in the compound represented by formula (III-a) and corresponds to a compound of formula (III-a) in which the ring A is a 2-pyridyl group, the ring B is a phenyl group and the ring C is a 2-cyanophenyl group.

The term "A crystal of 3-(2-cyanophenyl)-5-(2-pyridyl)-1-phenyl-1,2-dihydropyridin-2-one hydrate" is a crystal form of 3-(2-cyanophenyl)-5-(2-pyridyl)-1-phenyl-1,2-dihydropyridin-2-one containing water in the crystal, and as such, the amount of water contained in the crystal form is not particularly limited; it may be devoid of a portion of the water in the crystal. The term also encompasses the form wherein the water may coexist with adhesion water.

The term "crystal of 3-(2-cyanophenyl)-5-(2-pyridyl)-1-phenyl-1,2-dihydropyridin-2-one hydrate" means such a crystal form that it has preferably ½ to one molecule of water per one molecule of 3-(2-cyanophenyl)-5-(2-pyridyl)-1-phenyl-1,2-clihydropyridin-2-one in the crystal, may further contain 0 to ¼ molecules of adhesion water and may even be devoid of 0 to ½ molecules of water in the crystal.

Specifically, it means the following:

(1) A crystal of 3-(2-cyanophenyl)-5-(2-pyridyl)-1-phenyl-1,2-dihydropyridin-2-one ¾ hydrate;

(2) A crystal of 3-(2-cyanophenyl)-5-(2-pyridyl)-1-phenyl-1,2-dihydropyridin-2-one monohydrate (devoid of ¼ in the crystal);

(3) A crystal of 3-(2-cyanophenyl)-5-(2-pyridyl)-1-phenyl-1,2-dihydropyridin-2-one ½ hydrate coexisting with ¼ adhesion water; and (4) A crystal of 3-(2-cyanophenyl)-5-(2-pyridyl)-1-phenyl-1,2-dihydropyridin-2-one ½ hydrate; and (5) A crystal of 3-(2-cyanophenyl)-5-(2-pyridyl)-1-phenyl-1,2-dihydropyridin-2-one monohydrate.

The production method of the present invention is explained below in detail.

A Method for Producing a Compound of Formula (III) Represented by 3-(2-cyanophenyl)-5-(2-pyridyl)-1-phenyl-1,2-dihydropyridine-2-one (III-a)

This production method is characterized by converting a compound of formula (I) to the compound of formula (III) by reacting the compound of formula (I) with a compound of formula (II) in a solvent in the presence of a palladium compound, a copper compound and a phosphorus compound.

This reaction may be carried out also in a stream or atmosphere of an inert gas such as nitrogen, argon or the like.

As the compound (I), there can be used compounds producible by the method described in the production example 2 described hereinafter and "Chemical Society of Japan, Jikken Kagaku Koza (Experimental Chemistry) 19, 4th ed., Organic Synthesis I-Carbon Compounds.Halogen Compounds-", Maruzen Co., Ltd., Jun. 5, 1992, p 363-482, well-known compounds, purchasable compounds, and compounds easily producible from a purchasable compound by a method conventionally adopted by those skilled in the art.

As the compound (II), there can be used compounds producible by the method described in F. R. Bean et al., J. Am. Chem. Soc., 54, 4415(1932), J. M. Sugihara et al., J. Am. Chem. Soc., 80, 2443(1958), or the like, well-known compounds, purchasable compounds, and compounds easily producible from a purchasable compound by a method conventionally adopted by those skilled in the art.

The reaction is preferably carried out in a solvent. The solvent for reaction used is not particularly limited so long as it dissolves the starting materials to a certain degree and does not inhibit the reaction. As the solvent, there can be used, for example, organic solvents including ether solvents (e.g. tetrahydrofuran, 1,2-dimethoxyethane, diethyl ether and dioxane), aromatic hydrocarbon solvents (e.g. benzene, toluene and xylene), amide solvents (e.g. N,N-dimethylformamide, N,N-dimethylacetamide and N-methylpyrrolidone), dimethyl sulfoxide, etc.; and mixtures of any of these organic solvents and water. The solvent is suitably, for example, 1,2-dimethoxyethane or toluene.

The above term "palladium compound" means, for example, tetrakis(triphenylphosphine)palladium, tris(dibenzylideneacetone)dipalladium, bis(dibenzylideneacetone)palladium, tetrakis(tri-tert-butylphosphine)palladium, palladium acetate, dichlorobis(triphenylphosphine)palladium, dichlorobis(tri-o-tolylphosphine)palladium, dichlorobis(tricyclohexylphosphine)palladium, 1,1'-bis(diphenylphosphino)ferrocenedichloropalladium, palladium chloride, palladium hydroxide, palladium nitrate, di-µ-chlorobis(η-ally) palladium, bis(acetyl-acetonato)palladium, dichlorobis(benzonitrile)palladium, dichlorobis(acetonitrile)palladium or the like. The palladium compound is suitably palladium acetate, palladium chloride, palladium hydroxide or the like.

The above term "copper compound" means cuprous fluoride, cuprous chloride, cuprous bromide, cuprous iodide, cuprous acetate or the like. The copper compound is suitably cuprous bromide, cuprous iodide, cuprous chloride or cuprous acetate.

The above term "phosphorus compound" means, for example, triphenylphosphine, tri(2-methylphenyl)phosphine, bis(diphenylphosphino)methane, bis(diphenylphosphino)ethane, bis(diphenylphosphino)propane, bis(diphenylphosphino)butane, bis(diphenylphosphino)pentane, bis(diphenylphosphino)hexane, 2,2'-bis(diphenylphosphino)-1,1'-binaphthyl, tri-tert-butylphosphine, tri(4-methylphenyl) phosphine, tricyclohexylphosphine, 2-(di-tert-butylphosphino)biphenyl, 2-(dicyclohexylphosphino) biphenyl, 1,1'-bis(diphenyl-phosphino)ferrocene or the like. The phosphorus compound is suitably, for example, triphenylphosphine, tri-tert-butylphosphine or tri(4-methylphenyl)phosphine, more suitably triphenylphosphine or tri-tert-butylphosphine.

The above term "base" means an inorganic base such as sodium hydroxide, barium hydroxide, sodium carbonate, potassium carbonate, cesium carbonate, sodium hydrogencarbonate, potassium hydrogencarbonate, potassium phosphate, cesium fluoride, potassium fluoride or the like; an alkali metal alkoxide such as sodium ethoxide, sodium tert-butoxide, potassium tert-butoxide or the like; or an organic amine such as N-methylmorpholine, N,N-dimethylaniline, DBU, triethylamine or the like. The base is suitably, for example, sodium carbonate, potassium carbonate, cesium carbonate, sodium hydrogencarbonate or potassium hydrogencarbonate, more suitably sodium carbonate, potassium carbonate or cesium carbonate.

The reaction temperature is usually varied depending on the starting materials, the solvent and other reagents used in the reaction and is suitably 100° C. to 50° C. (the internal temperature of a reactor), more suitably 90° C. to 60° C. (the internal temperature of the reactor).

The reaction time is usually varied depending on the starting materials, the solvent, other reagents used in the reaction and the reaction temperature. It is suitable to conduct stirring for 1 to 10 hours, more suitably about 4 hours, in the above reaction temperature range after the addition of the reagents.

The compound (II) may be used in an amount of 1 to 10 moles, suitably 1 to 3 moles, more suitably 1.5 moles, per mole of the compound (I).

The above-mentioned palladium compound may be used in an amount of 0.001 to 0.1 mole, suitably 0.01 to 0.05 mole, more suitably 0.02 mole, per mole of the compound (I).

The above-mentioned copper compound may be used in an amount of 0.001 to 0.2 mole, suitably 0.01 to 0.1 mole, more suitably 0.05 mole, per mole of the compound (I).

The above-mentioned phosphorus compound may be used in an amount of 0.001 to 0.4 mole, suitably 0.01 to 0.2 mole, more suitably 0.05 to 0.1 mole, per mole of the compound (I).

The above-mentioned base may be used in an amount of 1 to 10 moles, suitably 1 to 5 moles, more suitably 1.5 moles, per mole of the compound (I).

It is known that in the Suzuki coupling, the addition of water to a reaction system gives a good result ("Efficient Synthesis of Losartan, A Nonpeptide Angiotensin II Receptor Antagonist", Robert D. Larsen et al., J. Org. Chem., 1994, 59, 6391-6394, "Investigation into the Suzuki-Miyaura coupling aiming at multikilogram synthesis of E2040 using (0-cyanophenyl)boronic esters", Y. Urawa et al., J. Organometallic Chemistry, 653(2002), 269-278). Also in the present invention, the same effect can be obtained by the addition of water. Water may be used in an amount of 1 to 20 moles, suitably 1 to 10 moles, more suitably 3 to 5 moles, per mole of the compound (I).

When made into a salt, 3-(2-cyanophenyl)-5-(2-pyridyl)-1-phenyl-1,2-dihydropyridine-2-one (III) may be stably isolated as substantially colorless crystals.

Preferable examples of the "salt" are hydrohalogenic acid salts such as hydrofluoride, hydrochloride, hydrobromide, hydroiodide, etc.; inorganic acid salts such as sulfate, nitrate, perchlorate, phosphate, etc.; and organic sulfonates such as methanesulfonate, trifluoromethane-sulfonate, ethanesulfonate, benzenesulfonate, toluenesulfonate, camphorsulfonate, etc. More preferable examples thereof are hydrohalogenic acid salts such as hydrofluoride, hydrochloride, hydrobromide, hydroiodide, etc.; and inorganic acid salts such as sulfate, nitrate, perchlorate, phosphate, etc. The most preferable examples thereof are hydrochloride, hydrofluoride and carbonate.

The crystal forms and production method thereof of the present invention is explained below in detail.

Crystal Forms of the Present Invention

The crystal forms of the present invention are crystal forms of the hydrate of Compound (A) with the characteristics described below. Although the respective measurement conditions for powder X-ray diffraction patterns and infrared absorption spectra (KBr method) are not particularly limited, the measurement should preferably be conducted under the measurement conditions for the powder X-ray diffraction patterns and the infrared absorption spectra (KBr method) as will be described below.

(1) A crystal having a diffraction peak at a diffraction angle (2θ±0.2°) of 8.7° in a powder X-ray diffraction;

(2) A crystal having a diffraction peak at a diffraction angle (2θ±0.2°) of 12.5° in a powder X-ray diffraction;

(3) A crystal having diffraction peaks at diffraction angles (2θ±0.2°) of 8.7° and 12.5° in a powder X-ray diffraction;

(4) A crystal having diffraction peaks at the diffraction angles (2θ±0.2°) shown in FIG. 4 or Table 5 below in a powder X-ray diffraction;

(5) A crystal having an absorption peak at a wavelength of 1588±1 $cm^{-1}$ in an infrared absorption spectrum (KBr method);

(6) A crystal having absorption peaks at wavelengths of 1588±1 $cm^{-1}$ and 751±1 $cm^{-1}$ in an infrared absorption spectrum (KBr method); and (7) A crystal having absorption peaks at the wavelengths ($cm^{-1}$) shown in FIG. 1 or Table 2 below in an infrared absorption spectrum (KBr method).

These characteristic peaks in the powder X-ray diffraction are not observable in the crystal form obtained by the production process disclosed in WO 01/96308 (see Reference Example 1, Table 4 and FIG. 3 as described below).

As for a diffraction angle (2θ) in the powder X-ray diffraction analysis, errors in the diffraction angle, generally, may occur within the range of ±0.2°. It is, therefore, to be understood that the values of the diffraction angles may include numerals on the order of ±0.2°. Accordingly, this invention encompasses not only crystal form having completely matching diffraction angles of the peaks in powder X-ray diffraction, but also crystal form having matching diffraction angles of the peaks within the errors of about ±0.2°.

Crystal of Hydrate

The term "having a diffraction peak at a diffraction angle (2θ±0.2°) of 8.7°" means "having a diffraction peak at a diffraction angle (2θ) of 8.5° to 8.9°." The term "having a diffraction peak at a diffraction angle (2θ±0.2°) of 12.5°" means "having a diffraction peak at a diffraction angle (2θ) of 12.3° to 12.7°."

The term "having an absorption peak at a wavenumber of 1588±1 $cm^{-1}$" means "having an absorption peak at a wavenumber of 1587 to 1589 $cm^{-1}$."

The term "having absorption peaks at wavenumbers of 1588±1 $cm^{-1}$ and 751±1 $cm^{-1}$" means "having absorption peaks at wavenumbers of 1587 to 1589 $cm^{-1}$ and of 750 to 752 $cm^{-1}$."

The term "having a peak at chemical shifts of around 146.7 ppm" means "having a peak substantially equivalent to 146.7 ppm when a $^{13}C$ Solid State NMR spectrum is measured under normal conditions or under the conditions substantially the same as those described in present specification." The term "having a peak at chemical shifts of around 123.3 ppm" means "having a peak substantially equivalent to 123.3 ppm when a $^{13}C$ Solid State NMR spectrum is measured under normal conditions or under the conditions substantially the same as those described in the present specification."

Anhydrous Crystal Form I

The term "having a diffraction peak at a diffraction angle (2θ±0.2°) of 10.3°" means "having a diffraction peak at a diffraction angle (2θ) of 10.1° to 10.5°." The term "having a diffraction peak at a diffraction angle (2θ±0.2° of 19.1°" means "having a diffraction peak at a diffraction angle (2θ) of 18.9° to 19.3°."

The term "having a peak at chemical shifts of around 149.0 ppm" means "having a peak substantially equivalent to 149.0 ppm when a $^{13}C$ Solid State NMR spectrum is measured under normal conditions or under the conditions substantially the same as those described in the specification." The term "having a peak at chemical shifts of around 125.6 ppm" means "having a peak substantially equivalent to 125.6 ppm when a $^{13}C$ Solid State NMR spectrum is measured under normal conditions or under the conditions substantially the same as those described in the present specification."

Anhydrous Crystal Form V

The term "having a diffraction peak at a diffraction angle (2θ±0.2°) of 16.7°" means "having a diffraction peak at a diffraction angle (2θ) of 16.5° to 16.9°." The term "having a diffraction peak at a diffraction angle (2θ±0.2° of 12.9°" means "having a diffraction peak at a diffraction angle (2θ) of 12.7° to 15 13.1°." The term "having a diffraction peak at a diffraction angle (2θ±0.2° of 24.9°" means "having a diffraction peak at a diffraction angle (2θ) of 24.7° to 25.1°."

The term "having an absorption peak at a wavenumber of 1658±1 cm$^{-1}$" means "having an absorption peak at a wavenumber of 1657 to 1659 cm$^{-1}$."

The term "having an absorption peak at a wavenumber of 501±1 cm$^{-1}$" means "having an absorption peak at a wavenumber of 500 to 502 cm$^{-1}$."

The term "having a peak at chemical shifts of around 145.9 ppm" means "having peak substantially equivalent to 145.9 ppm when a $^{-3}$C Solid State NMR spectrum is measured under normal conditions or under the conditions substantially the same as those described in the specification." The term "having a peak at chemical shifts of around 137.7 ppm" means "having a peak substantially equivalent to 137.7 ppm when a $^{13}$C Solid State NMR spectrum is measured under normal conditions or under the conditions substantially the same as those described in the present specification."

Anhydrous Crystal Form III

The term "having a diffraction peak at a diffraction angle (2θ±0.2°) of 23.7°" means "having a diffraction peak at a diffraction angle (2θ) of 23.5° to 23.9°." The term "having a diffraction peak at a diffraction angle (2θ±0.2°) of 25.0°" means "having a diffraction peak at a diffraction angle (2θ) of 24.8° to 25.2°." The term "having a diffraction peak at a diffraction angle (2θ±0.2°) of 5.7°" means "having a diffraction peak at a diffraction angle (2θ) of 5.5° to 5.9°." The term "having a diffraction peak at a diffraction angle (2θ±0.2°) of 9.5°" means "having a diffraction peak at a diffraction angle (2θ) of 9.3° to 9.7°."

The term "an alkyl ketone solvent" means an organic solvent of dialkyl ketone such as acetone and ethyl methyl ketone, and preferably acetone.

The term "an alcoholic solvent" means an organic solvent of $C_{1-6}$ alcohol, such as methanol, ethanol, 1-propanol and 2-propanol, and preferably methanol or 1-propanol.

The term "under reduced pressure" is not particularly limited insofar as it is 760 mmHg or less; and it is preferably from 760 to 0.1 mmHg, more preferably from 50 to 0.1 mmHg, and most preferably from 30 to 5 mmHg.

The production methods of the crystal forms of the present invention are explained below in detail.

General Production Process for Crystal of Hydrate

The crystal of hydrate of the present invention can be stably produced on an industrial scale by preparing Compound (A) according to Example 7 in WO 01/96308 or Example 1 as described herein below, dissolving Compound (A) in a specific solvent by heating, and crystallizing it by cooling at stirring.

Compound (A) to be used in the crystallization may be any form of hydrate, anhydrous, amorphous and crystalline forms which includes plural crystal polymorphs, and may even be a mixture of the foregoing.

The solvents to be used in the crystallization include one member or a mixed solvent of two members selected from the group consisting of an alcoholic solvent, an alkyl ketone solvent, and water. The solvent is preferably a mixed solvent of acetone and water.

When the mixed solvent of acetone and water is used, its mixing ratio (volume ratio) is preferably from 37:3 to 24:16, more preferably from 9:1 to 7:3, and further more preferably about 8:2. The most preferred is a mixed solvent formed by dissolving the crystals in a mixed solvent of acetone and water (9:1) and thereafter adding water to the mixed solvent to prepare a solution of acetone and water (8:2).

The amount of the solvent used may appropriately be selected between the lower limit and the upper limit, the lower limit being an amount to dissolve Compound (A) by heating and the upper limit being an amount so as not to significantly reduce the yield of the crystals. The amount of crystallization solvent is preferably from 10- to 50-fold (v/w) as a volume ratio based on the weight of Compound (A), more preferably from 30- to 50-fold (v/w). Further preferably, the amount is about 40-fold (v/w) if acetone-water (9:1) is used; and it is about 45-fold (v/w) if acetone-water (8:2) is used.

The temperature at which Compound (A) is dissolved by heating may appropriately be selected as the temperature to dissolve Compound (A1) depending on the solvent. The temperature is preferably from the reflux temperature of the crystallization solvent to 50° C., more preferably from 65 to 55° C.

Any change in the cooling rate during crystallization may produce crystals with different forms (polymorphisms). It is, therefore, desired that the crystallization be performed by suitably adjusting the cooling rate in consideration of possible effects on the quality and the particle size of the crystals or the like. Cooling is preferably performed at a rate of 40 to 5° C. per hour and more preferably at a rate of 25 to 15° C. per hour.

The final crystallization temperature may also appropriately be selected in consideration of the yield and the quality of the crystals, or the like; and it is preferably from 10 to −25° C.

In the crystallization, seed crystals may or may not be added, which comprise a small amount of crystals of 3-(2-cyanophenyl)-5-(2-pyridyl)-1-phenyl-1,2-dihydropyridin-2-one hydrate. There is no particular limitation to the temperature at which the seed crystals are added. The temperature is preferably 60° C. or less, more preferably from 55 to 0° C., further more preferably from 55 to 35° C., and most preferably about 40° C.

The precipitated crystals can be separated by usual filtration, washed with solvent if necessary, and then dried to produce the desired crystals. The solvent for use in washing the crystals is common to the crystallization solvent, and it is preferably a mixed solvent of acetone-water (9:1 to 1:1), more preferably a mixed solvent of acetone-water (about 1:1).

Drying Method for Crystals

The crystals separated by the filtration can be dried by allowing them to stand in the atmosphere, where appropriate, or by heating.

The time during which the residual solvent is removed below the prescribed amount may appropriately be selected as the drying time, depending on the production quantity, the drying apparatus, the drying temperature or the like. Drying can be performed either under aeration or under reduced pressure. The level of pressure reduction may appropriately be selected, depending on the production quantity, the drying apparatus, the drying temperature or the like. The obtained crystals may be allowed to stand in the atmosphere after drying if necessary.

The crystals produced by the above-mentioned process comprise a homogeneous crystal form. Being provided with the preferable properties such that it is stable, has no tendency to readily transform into other crystal or amorphous forms, and is not hygroscopic, these crystals are suited to formulation.

The use of Compound (A) as a therapeutic agent for neurodegenerative diseases or others is fully disclosed in WO 01/96308. The crystal forms of the invention can be used as the active ingredient in the therapeutic agent for neurodegenerative diseases or others. The entire disclosure of WO 01/96308 is thus hereby incorporated by reference.

When Compound (A) of the present invention is to be used as a medicament, it is normally compounded with suitable pharmaceutical ingredients to prepare pharmaceutical products for use. Notwithstanding, the use of a drug substance form of the compound of the invention as a medicament should not be negated.

The pharmaceutical ingredients may include excipients, binders, lubricants, disintegrating agents, coloring agents, taste correctives, emulsifiers, surfactants, dissolving aids, suspending agents, isotonizing agents, buffering agents, preservatives, antioxidants, stabilizers, absorption enhancers, and the like, all of which are generally used in medicaments. If desired, these agents may be combined for use.

The excipients may include, for example, lactose, white soft sugar, glucose, corn starch, mannitol, sorbitol, starch, alpha starch, dextrin, crystalline cellulose, light silicic anhydride, aluminum silicate, calcium silicate, magnesium aluminometasilicate, calcium hydrogenphosphate, and the like.

The binders may include, for example, polyvinyl alcohol, methylcellulose, ethylcellulose, gum Arabic, tragacanth, gelatin, shellac, hydroxypropylmethylcellulose, hydroxypropylcellulose, carboxymethylcellulose sodium, polyvinylpyrrolidone, macrogol, and the like.

The lubricants may include, for example, magnesium stearate, calcium stearate, sodium stearyl fumarate, talc, polyethylene glycol, colloidal silica, and the like.

The disintegrating agents may include, for example, crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch, carboxymethyl starch sodium, and the like.

The coloring agents may include iron sesquioxide, yellow iron sesquioxide, carmine, caramel, beta-carotene, titanium oxide, talc, riboflavin sodium phosphate, yellow aluminum lake, and the like, which have been approved as additives for medicaments.

The taste correctives agents may include cocoa powder, menthol, aromatic powder, mentha oil, borneol, powdered cinnamon bark, and the like.

The emulsifiers or the surfactants may include stearyl triethanolamine, sodium lauryl sulfate, lauryl aminopropionic acid, lecithin, glycerin monostearate, sucrose fatty acid ester, glycerin fatty acid ester, and the like.

The dissolving aids may include polyethylene glycol, propylene glycol, benzyl benzoate, ethanol, cholesterol, triethanolamine, sodium carbonate, sodium citrate, Polysorbate 80, nicotinamide, and the like.

The suspending agents may include, in addition to the surfactants, hydrophilic polymers such as polyvinyl alcohol, polyvinylpyrrolidone, methylcellulose, hydroxymethylcellulose, hydroxyethylcellulose, and hydroxypropylcellulose.

The isotonizing agents may include glucose, sodium chloride, mannitol sorbitol and the like.

The buffering agents may include the buffers of phosphate, acetate, carbonate, citrate and the like.

The preservatives may include methylparaben, propylparaben, chlorobutanol, benzyl alcohol, phenethyl alcohol, dehydroacetic acid, sorbic acid and the like. The antioxidants may include sulfite, ascorbic acid, alpha-tocopherol and the like.

The stabilizers may include those generally used in medicaments.

The absorption enhancers may include those generally used in medicaments.

The pharmaceutical products described above may include: oral agents such as tablets, powders, granules, capsules, syrups, troches, and inhalations; external preparations such as suppositories, ointments, ophthalmic ointments, tapes, ophthalmic solutions, nasal drops, ear drops, poultices, and lotions; and injections.

The oral agents may appropriately be combined with the auxiliaries described above to form preparations. In addition, the surfaces of the agents may be coated if necessary.

The external preparations may appropriately be combined with the auxiliaries, in particular, excipients, binders, taste correctives, emulsifiers, surfactants, dissolving aids, suspending agents, isotonizing agents, preservatives, antioxidants, stabilizers, or absorption enhancers to form the preparations.

The injections may appropriately be combined with the auxiliaries, in particular, emulsifiers, surfactants, dissolving aids, suspending agents, isotonizing agents, preservatives, antioxidants, stabilizers, or absorption enhancers to form the preparations.

When Compound (A) of the present invention is to be used as a medicament, its dosage level may differ depending on the symptoms, ages or others. Compound (A) is normally given in a single administration or in divided administrations 2 to 6 times daily at the following doses: from 0.05 to 10 mg (preferably from 0.1 to 5 mg) in the case of an oral agent; from 0.01 to 10 mg (preferably from 0.05 to 5 mg) in the case of an external preparation; and 0.01 to 5 mg in the case of an injection. Here, the actual amounts to be administered are indicated with respect to the oral agent and the injection, while the amount to be absorbed by the body is indicated with respect to the external preparation.

The preparations for therapeutic or prophylactic use in humans containing crystal of 3-(2-cyanophenyl)-5-(2-pyridyl)-1-phenyl-1,2-dihydropyridin-2-one hydrate (Compound (A)) according to the invention may be obtained by the general methods that are accepted in manufacturing pharmacy. The specific formulation examples of preparations are shown below.

The compound of the present invention [i.e., 3-(2-cyanophenyl)-5-(2-pyridyl)-1-phenyl-1,2-dihydropyridin-2-one], lactose, low-substituted hydroxypropylcellulose were blended. Polyvinylpyrrolidone dissolved in an appropriate amount of purified water was then used to wet granulate the blend. These granulates were dried and then size-controlled. Low-substituted Hydroxypropylcellulose and magnesium stearate were blended to the resulting granulates, after which they was tabletted. The obtained tablets were film-coated with an aqueous solution of the coating base (a mixture of hydroxypropylmethylcellulose, talc, Macrogol 6000, titanium oxide and yellow iron sesquioxide). The amounts of the respective materials to be used per tablet are shown in Table 1 below.

TABLE 1

| Material | Purpose | 0.5 mg tablet | 1.0 mg tablet | 2.0 mg tablet |
| --- | --- | --- | --- | --- |
| compound of the invention*1 | principle agent | 0.5 mg | 1.0 mg | 2.0 mg |
| lactose | excipient | 80.0 mg | 79.5 mg | 78.5 mg |
| low-substituted hydroxypropylcellulose | disintegrator | 9.0 mg | 9.0 mg | 9.0 mg |
| polyvinylpyrrolidone | binder | 5.0 mg | 5.0 mg | 5.0 mg |

TABLE 1-continued

| Material | Purpose | 0.5 mg tablet | 1.0 mg tablet | 2.0 mg tablet |
|---|---|---|---|---|
| low-substituted hydroxypropylcellulose | disintegrator | 5.0 mg | 5.0 mg | 5.0 mg |
| magnesium stearate | lubricant | 0.5 mg | 0.5 mg | 0.5 mg |
| purified water | solvent | q.s. | q.s. | q.s. |
| coating base*[2] | coating agent | 5.0 mg | 5.0 mg | 5.0 mg |
| purified water | solvent | q.s. | q.s. | q.s. |
| total | | 105 mg | 105 mg | 105 mg |

*[1]3-(2-Cyanophenyl)-5-(2-pyridyl)-1-phenyl-1,2-dihydropyridin-2-one (Hydrate)
*[2]Mixture of hydroxypropylmethylcellulose, talc, Macrogol 6000, titanium oxide and yellow iron sesquioxide The present invention is explained below in further detail with working examples but they are merely for illustration and the production method of the present invention is not limited in any case by the following specific examples. Those skilled in the art may conduct the present invention to maximum by making various modifications to not only the following working examples but also the claims in the present specification, and these modifications are included in the claims in the present specification.

Example 1

Synthesis of 3-(2-cyanophenyl)-5-(2-pyridyl)-1-phenyl-1,2-dihydropyridine-2-one (1) Synthesis of 5-(2-pyridyl)-1-phenyl-1,2-dihydropyridine-2-one

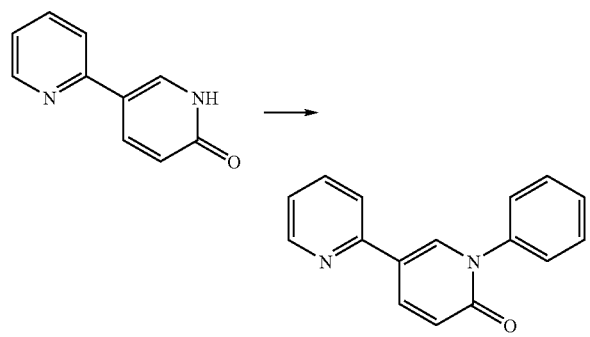

After the inner atmosphere of a reactor was replaced with nitrogen, a mixture of 5-(2-pyridyl)-1,2-dihydropyridine-2-one (WO2004/009553) (7.33 kg), triphenylboroxine (9.0 kg), copper acetate (anhydrous) (0.80 kg), water (0.50 kg), pyridine (7.1 kg) and N,N-dimethylformamide (66.7 kg) was stirred for 1 hour in the reactor at an internal temperature of 28° C.

While introducing air adjusted to an oxygen concentration of 9% with nitrogen into the reactor at a rate of 30 L/min, the reaction mixture was stirred for 16 hours at 39° C. to 40° C. (internal temperature) to obtain a reaction mixture 1A.

Water (191 kg) and 25% aqueous ammonia (85.8 kg) were placed in another reactor and cooled to 8.7° C. with cold water. Then, the above-mentioned reaction mixture 1A was added thereto over a period of 3 minutes. The resulting reaction mixture was stirred for 4 hours while being cooled with cold water. The precipitate in the reaction mixture was collected by filtration by the use of a centrifuge and washed with 65 kg of water.

The precipitate, water (97 kg) and 25% aqueous ammonia (43.5 kg) were placed in a reactor and stirred for 1 hour while being kept warm with warm water at 25° C. The precipitate in the reaction mixture was collected by filtration by the use of a centrifuge, washed with 32.6 kg of water and then dried under reduced pressure (60° C., 18 hours) to obtain 9.6 kg of 5-(2-pyridyl)-1-phenyl-1,2-dihydropyridine-2-one.

$^1$H NMR (400 MHz, DMSO-$d_6$) δ 8.61-8.50 (m, 1H), 8.36 (d, 1H), 8.29 (dd, 1H), 7.90 (d, 1H), 7.80 (ddd, 1H), 7.56-7.45 (m, 5H), 7.27 (dd, 1H), 6.62 (d, 1H).

(2) Synthesis of 3-bromo-5-(2-pyridyl)-1-phenyl-1,2-dihydropyridine-2-one

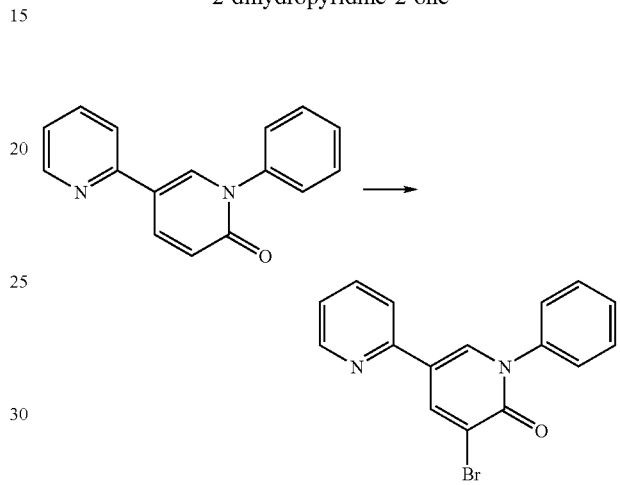

5-(2-Pyridyl)-1-phenyl-1,2-dihydropyridine-2-one (200 g), N-bromosuccinimide (157.7 g) and ethyl acetate (4 L) were placed in a 10-L reactor, and the reaction mixture was stirred at 30° C. (external temperature) in a nitrogen stream for 9 hours and 20 minutes. A 3% aqueous hydrosulfite solution (2 L) and toluene (2 L) were added to the reaction mixture, followed by stirring at 55° C. (external temperature) for 30 minutes. After completion of the reaction, the aqueous layer (the lower layer) in the reaction mixture was separated. Then, the organic layer was washed four times with water (2 L), and the organic solvent was removed under reduced pressure with stirring.

Thereafter, 1,2-dimethoxyethane (4 L) was added to the residue and the resulting mixture was concentrated under reduced pressure to obtain crude 3-bromo-5-(2-pyridyl)-1-phenyl-1,2-dihydropyridine-2-one.

(3) Synthesis of 3-(2-cyanophenyl)-5-(2-pyridyl)-1-phenyl-1,2-dihydropyridine-2-one

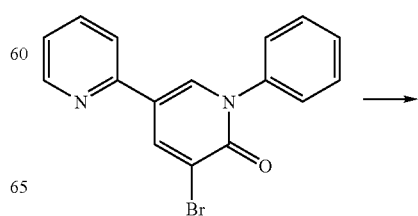

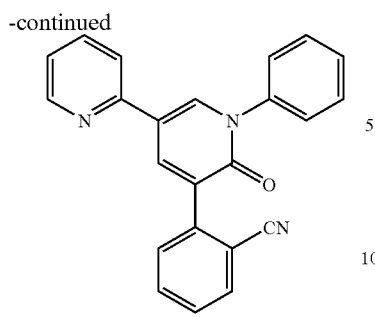

2-(1,3,2-Dioxaborinan-2-yl)benzonitrile (214.9 g), palladium acetate (3.44 g), triphenylphosphine (16.07 g), cuprous iodide (7.29 g), 1,2-dimethoxyethane (3.1 L) and potassium carbonate (158.8 g) were placed in a reactor containing the whole of the crude 3-bromo-5-(2-pyridyl)-1-phenyl-1,2-dihydropyricline-2-one obtained as concentration residue in the above item (2), and the resulting mixture was stirred with heating at 70° C. (external temperature) for 30 minutes under a nitrogen atmosphere and then stirred with heating under reflux for 4 hours.

Thereafter, ethyl acetate (2.5 L) was added to the reaction mixture at 70° C. (external temperature) and stirred for 10 minutes. The resulting reaction mixture was filtered and the precipitate was washed with ethyl acetate (2.5 L). The whole of the filtrate thus obtained was transferred into a reactor and 12.5% aqueous ammonia (5 L) was added thereto, followed by stirring at 60° C. (external temperature) for 53 minutes. The lower layer (the aqueous layer) in the reaction mixture was separated. A 5% aqueous sodium chloride solution (2.5 L) and 25% aqueous ammonia (2.5 L) were added to the remaining organic layer and stirred. Thereafter, the lower layer (the aqueous layer) was separated and a 5% aqueous sodium chloride solution (5 L) was added to the remaining organic layer and stirred, and then the lower layer (the aqueous layer) was separated. The remaining organic layer was concentrated under reduced pressure, followed by adding thereto 4 L of acetone, and the resulting mixture was concentrated under reduced pressure.

Acetone (7.2 L) and water (0.8 L) were added to the residue and the resulting mixture was stirred at 60° C. (external temperature) for 1 hour and 10 minutes to effect dissolution. The resulting solution was cooled with stirring at 38° C. (external temperature) for 18 minutes. To the reaction mixture was added 1 g of seed crystals (crystals of hydrate of 3-(2-cyanophenyl)-5-(2-pyridyl)-1-phenyl-1,2-dihydropyridine-2-one) at an internal temperature of 40° C., and the resulting mixture was stirred at 35° C. (external temperature) for 30 minutes. Thereafter, the reaction mixture was stirred while lowering the external temperature by 5° C. at intervals of 30 minutes. At an external temperature of 10° C., the reaction mixture was stirred for 17 hours.

Water (2.29 L) was added dropwise to the reaction mixture with stirring over a period of 3 hours and 10 minutes. After completion of the dropwise addition, the resulting mixture was stirred for another 1 hour and 20 minutes. The reaction mixture was filtered and the precipitate was washed with 2 L of 50% acetone-water to obtain 3-(2-cyanophenyl)-5-(2-pyridyl)-1-phenyl-1,2-dihydropyridine-2-one (526.28 g) as a wet cake (dry weight: 168.3 g).

(4) Conversion of 3-(2-cyanophenyl)-5-(2-pyridyl)-1-phenyl-1,2-dihydropyridin-2-one in the Wet Cake to Dried Weight The obtained wet cake (4.378 g) was weighed out and dried under reduced pressure at 50° C. for 4 hours to give 1.4005 g of a dried powder.

Converted value as dried weight=(1.4005/4.378)×526.28=168.3 g (5) Determination of Acetone and Water Weight Contents in the Wet Cake of 3-(2-cyanophenyl)-5-(2-pyridyl)-1-phenyl-1,2-dihydro-pyridin-2-one Gas chromatographic analysis of the obtained wet cake under the conditions described below ascertained that the wet cake obtained in (3) above contained 168 mL of acetone and 186 mL of water.

Gas Chromatographic Analysis Conditions:

Column: DB-WAX (30 m×0.53 mm, 1 µm); Detector: TCD;

Oven temp.: 60° C. (8 min), 60-180° C. (70° C./min), 180° C. (5 min);

Detector temp.: 210° C.; inlet temp.: 150° C.; Column flow: 5.0 mL/min; split ratio: (1:4); Injection vol.: 2 µL Example 2

Synthesis of 3-(2-cyanophenyl)-5-(2-pyridyl)-1-phenyl-1,2-dihydropyridine-2-one (1) Synthesis of 3-bromo-5-(2-pyridyl)-1-phenyl-1,2-dihydropyridine-2-one

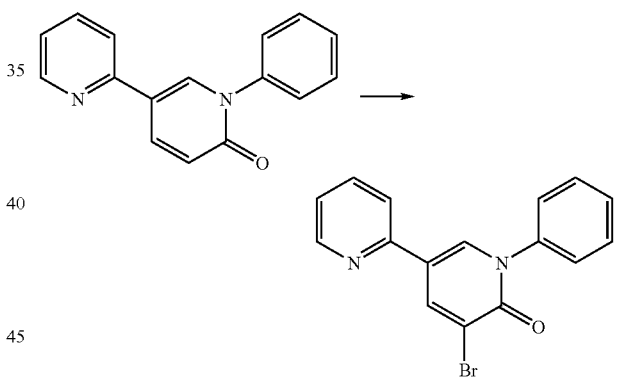

5-(2-Pyridyl)-1-phenyl-1,2-dihydropyridine-2-one (300 g), N-bromosuccinimide (236.5 g) and N,N-dimethylformamide (1.8 L) were placed in a 10-L reactor, and the reaction mixture was stirred at 30° C. (external temperature) in a nitrogen stream for 3 hours and 15 minutes. 2-Propanol (4.2 L) was added dropwise to the reaction mixture over a period of 9 minutes, followed by adding thereto water (2.1 L) over a period of 7 minutes. The resulting mixture was heated at 85° C. (external temperature) with stirring. After confirming the dissolution of the contents, the resulting solution was stirred at an external temperature of 55° C. for 1 hour. Thereafter, the solution was stirred at 40° C. (external temperature) for another 22 minutes, at 30° C. (external temperature) for further another 23 minutes, and then at 10° C. (external temperature) for still another 15 hours and 15 minutes. The reaction mixture was filtered and the precipitate was washed with 50% 2-propanol-water (2.4 L) and then dried under reduced pressure (60° C., 6 hours) to obtain 341.45 g of 3-bromo-5-(2-pyridyl)-1-phenyl-1,2-dihydropyridine-2-one. Yield: 86.4%.

¹H NMR (400 MHz, CDCl₃) δ 8.59-8.56 (m, 1H), 8.50 (d, 1H), 8.18 (d, 1H), 7.72 (td, 1H), 7.53-7.41 (m, 6H), 7.20 (ddd, 1H).

(2) Synthesis of 3-(2-cyanophenyl)-5-(2-pyridyl)-1-phenyl-1,2-dihydropyridine-2-one

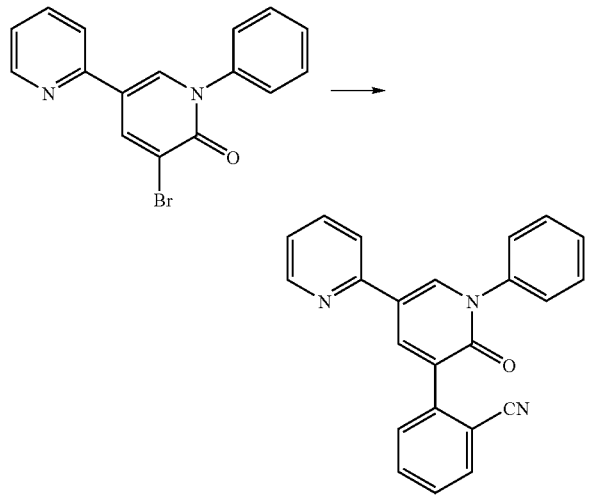

3-Bromo-5-(2-pyridyl)-1-phenyl-1,2-dihydropyridine-2-one (100 g), 2-(1,3,2-dioxaborinan-2-yl)benzonitrile (85.7 g), palladium acetate (1.37 g), triphenylphosphine (6.4 g), cuprous iodide (2.91 g), 1,2-dimethoxyethane (1.25 L) and potassium carbonate (63.4 g) were placed in a 3-L reactor, and pressure reduction and the replacement of the air in the reaction system with nitrogen by repressurization with nitrogen were carried out 10 times. The reaction mixture was stirred with heating (in an oil bath at 100° C.) under a nitrogen atmosphere for 3 hours and 40 minutes.

Thereafter, ethyl acetate (750 mL) was added to the reaction mixture and the resulting mixture was filtered. The precipitate was washed with ethyl acetate (750 mL). To the filtrate thus obtained were added 750 mL of water and 25% aqueous ammonia (250 mL), and the resulting mixture was stirred at 60° C. (external temperature) for 30 minutes. The lower layer (the aqueous layer) in the reaction mixture was separated. A 2.5% aqueous sodium chloride solution (370 mL), 25% aqueous ammonia (130 mL) and 1,2-dimethoxyethane (500 mL) were added to the remaining organic layer, followed by stirring at 60° C. (external temperature) for 10 minutes. Thereafter, the lower layer (the aqueous layer) was separated and a 2.5% aqueous sodium chloride solution (370 mL), 25% aqueous ammonia (130 mL) and 1,2-dimethoxyethane (200 mL) were added to the remaining organic layer and stirred for 10 minutes, and then the lower layer (the aqueous layer) was separated. A 2.5% aqueous sodium chloride solution (500 mL) and 1,2-dimethoxyethane (200 mL) were added to the remaining organic layer, followed by stirring at 60° C. (external temperature) for 10 minutes. Thereafter, the lower layer (the aqueous layer) was separated. The remaining organic layer was concentrated under reduced pressure (external temperature: 65° C.), followed by adding thereto 2 L of acetone, and the resulting mixture was concentrated under reduced pressure (external temperature: 60° C.).

Acetone (2.88 L) and water (320 mL) were added to the residue and the resulting mixture was stirred at 55° C. (external temperature) for 1 hour and 10 minutes to effect dissolution. The resulting solution was cooled with stirring at 38° C. (external temperature) for 38 minutes. To the reaction mixture was added 500 mg of seed crystals (crystals of hydrate of 3-(2-cyanophenyl)-5-(2-pyridyl)-1-phenyl-1,2-dihydropyridine-2-one) at an internal temperature of 40° C., and the resulting mixture was stirred for 1 hour at an external temperature changed to 30° C. This mixture was stirred for 1 hour at an external temperature changed to 20° C. and then stirred for 1 hour and 20 minutes at an external temperature of 8° C.

Water (915 mL) was added dropwise to the reaction mixture with stirring over a period of 2 hours and 50 minutes. After completion of the dropwise addition, the resulting mixture was stirred for another 14 hours. The reaction mixture was filtered and the precipitate was washed with 500 mL of 50% acetone-water and then 500 mL of water to obtain 3-(2-cyanophenyl)-5-(2-pyridyl)-1-phenyl-1,2-dihydropyricline-2-one (251.5 g) as a wet cake (dry weight: 83.3 g).

¹H NMR (400 MHz, DMSO-d₆) δ 8.61-8.57 (m, 1H), 8.52 (d, 1H), 8.47 (d, 1H), 8.00 (d, 1H), 7.92 (d, 1H), 7.83 (td, 1H), 7.78 (t, 1H), 7.74-7.70 (d-like, 1H), 7.61-7.48 (m, 6H), 7.29 (dd, 1H).

Example 3

Synthesis of 3-(2-cyanophenyl)-5-(2-pyridyl)-1-phenyl-1,2-dihydropyridine-2-one

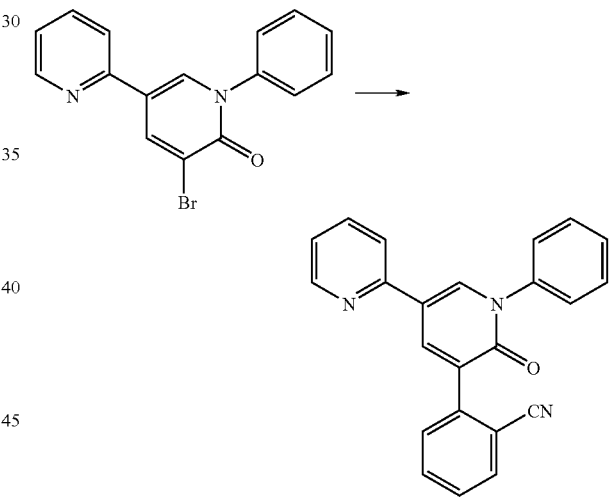

3-Bromo-5-(2-pyridyl)-1-phenyl-1,2-dihydropyridine-2-one (188 g), 2-(1,3,2-dioxaborinan-2-yl)benzonitrile (161.2 g), palladium acetate (2.58 g), triphenylphosphine (12.07 g), 1,2-dimethoxyethane (2.82 L) and ion-exchanged water (41.4 mL) were placed in a 5-L reactor, and pressure reduction and the replacement of the air in the reaction system with nitrogen by repressurization with nitrogen were carried out 5 times with stirring. Potassium carbonate (119.14 g) was added to the reaction mixture and pressure reduction and the replacement of the air in the resulting mixture with nitrogen by repressurization with nitrogen were carried out 5 times. Then, the reaction mixture was stirred with heating (in an oil bath at 95° C.) under reflux in a nitrogen atmosphere for 1 hour and 49 minutes.

Thereafter, the oil bath was removed and ethyl acetate (800 mL) was added to the reaction mixture at 65.4° C. (internal temperature). The resulting mixture was filtered and the precipitate was washed with ethyl acetate (2.4 L). The filtrate (5.28 kg) thus obtained was divided into halves (2.64 kg×2) and each half was transferred into a 5-L reactor. Trimercaptotriazine (3.05 g) and ethyl acetate (380 mL) were placed in each of the reactors and the reaction mixture was stirred at 50° C. (the external temperature in an oil bath) for 13 hours and 10 minutes. The two solutions thus obtained were filtered in succession by the use of Celite (94 g) previously rinsed with methanol (1 L) and ethyl acetate (1 L) and the precipitate was rinsed with a 4:3 mixture (1.35 L) of ethyl acetate and 1,2-dimethoxyethane. The filtrate thus obtained was transferred into a 20-L separator and hydrochloric acid prepared from concentrated hydrochloric acid (700 mL) and ion-exchanged water (4.2 L) was added to the filtrate. After stirring at 37.6° C. (internal temperature) for 8 minutes, the aqueous layer (the lower layer) was separated. Then, 2N-hydrochloric acid (3.8 L) was added to the organic layer, followed by stirring at 39.3° C. (internal temperature) for 8 minutes, and the aqueous layer (the lower layer) was separated. Ethyl acetate (3 L) was added to the combined aqueous layer and stirred for 8 minutes, and then ethyl acetate (3 L) was added thereto and stirred for 5 minutes. Thereafter, the aqueous layer (the lower layer) was separated. This aqueous layer was cooled to 20° C. (internal temperature) with stirring in a cold-water bath, and then 25% aqueous ammonia (2.25 L) was added dropwise thereto over a period of 27 minutes with cooling in an ice-water bath. The resulting mixture was stirred for another 3 hours and 26 minutes. The reaction mixture was filtered under reduced pressure and the precipitate was washed with ion-exchanged water (3 L). The washed precipitate was dried by air blowing (60° C., 16 hours and 6 minutes) to obtain 3-(2-cyanophenyl)-5-(2-pyridyl)-1-phenyl-1,2-dihydropyridine-2-one (162.62 g).

$^1$H NMR (400 MHz, DMSO-$d_6$) δ 8.60-8.57 (m, 1H), 8.53 (d, 1H), 8.47 (d, 1H), 8.00 (d, 1H), 7.92 (d, 1H), 7.83 (td, 1H), 7.78 (t, 1H), 7.72 (d, 1H), 7.61-7.48 (m, 6H), 7.30 (dd, 1H).

Example 4

Crystallization of 3-(2-cyanophenyl)-5-(2-pyridyl)-1-phenyl-1.2-dihyydropyridin-2-one (Hydrate crystal)

A 10 L-flask was charged with 526.28 g of 3-(2-cyanophenyl)-5-(2-pyridyl)-1-phenyl-1,2-dihydropyridin-2-one obtained as the wet cake in (3) of Example 1. Out of an acetone-water prepared from 5890 mL of acetone and 490 mL of water, 5.5 L was added to the flask and heated. Filtration was carried out after dissolution. While the 10-L flask and the filtrated residue were washed with the remaining total of the acetone water, all the filtrate was transferred to a 10-L flask.

The mixture was stirred at an external temperature of 40° C., and after the internal temperature reached 40° C., the external temperature was adjusted to 35° C. Next, 842 mg of 3-(2-cyanophenyl)-5-(2-pyridyl)-1-phenyl-1,2-dihydropyridin-2-one hydrate was added to the mixture. After stirring the mixture for 30 minutes, the external temperature was changed to 30° C., and then to 25° C. after 30 minutes. The external temperature was lowered by 5° C. every 30 minutes thereafter to as low as 15° C. After stirring the mixture at an external temperature of 15° C. for 30 minutes, the external temperature was further lowered to 8° C. and stirring continued for 1 hour.

To the mixture was added dropwise 842 mL of water at 11° C. (internal temperature) over a period of 1 hour and 10 minutes. One hour after the completion of addition, the external temperature was changed to 0° C. and the mixture was stirred for 40 minutes. The external temperature was then lowered to −20° C. and stirring continued for 15 hours.

The precipitates in the mixture were collected by filtration. After the precipitates were washed with 1700 mL of 50% acetone-water, they were dried under aeration for 50 minutes. Subsequently, these precipitates were dried with a vibration drier at 40° C. under reduced pressure for 11 hours and were additionally dried at 60° C. for 3 hours.

After the temperature of the drier was cooled to room temperature, the external atmosphere was aspirated into the drier at 950 hpa for 4 hours to give 172.4 g of 3-(2-cyanophenyl)-5-(2-pyridyl)-1-phenyl-1,2-dihydropyridin-2-one (crystal form of the hydrate).

$^1$H NMR (400 MHz, DMSO-$d_6$): δ 8.61-8.57 (m, 1H), 8.53-8.52 (d-like, 1H), 8.47 (d, 1H), 8.01 (d, 1H), 7.92 (d, 1H), 7.86-7.81 (t-like, 1H), 7.79-7.76 (t-like, 1H), 7.72 (d, 1H), 7.61-7.48 (m, 6H), 7.31-7.28 (m, 1H).

Residual palladium: 15 ppm

Reference Example 1

Production Anhydrous Crystals of 3-(2-cyanophenyl)-5-(2-pyridyl)-1-phenyl-1,2-dihydopyridin-2-one (Anhydrous Crystal Form II)

In the same manner as the procedure after reaction work-up that are described in Example 7 in WO 01/96308, the production was carried out below. The synthetic method for 3-(2-cyanophenyl)-5-(2-pyridyl)-1-phenyl-1,2-dihydropyridin-2-one [alternative name: 2-(2-oxo-1-phenyl-5-(pyridin-2-yl)-1,2-dihydropyridin-3-yl)benzonitrile] is described in Example 7 in WO 01/96308 as well as in Example 1 herein above.

Ethyl acetate (400 mL) was added to 3-(2-cyanophenyl)-5-(2-pyridyl)-1-phenyl-1,2-dihydropyridin-2-one (8 g). The mixture was heated at 60° C. in a warm bath. Additional acetate (160 mL) was added to the mixture and the solids were dissolved by heating at 70° C. in the warm bath. After n-hexane (80 mL) was added to this solution, the solvent was evaporated under reduced pressure to give 7.7 g of a pale yellow powder.

$^1$H NMR (400 MHz, DMSO-$d_6$): δ 8.59-8.57 (m, 1H), 8.53 (d, 1H), 8.47 (d, 1H), 8.01 (d, 1H), 7.92 (d, 1H), 7.83 (ddd, 1H), 7.80-7.76 (m, 1H), 7.73-7.71 (d-like, 1H), 7.61-7.48 (m, 6H), 7.30 (dd, 1H).

Example 5

Production of Crystals of 3-(2-cyanophenl)-5-(2-pyridyl)-1-phennyl-1,2-dihydropyridin-2-one hydrate (Hydrate Crystal)

A 500 mL-egg plant vessel was charged with 7 g of 3-(2-cyanophenyl)-5-(2-pyridyl)-1-phenyl-1,2-dihydropyridin-2-one. To the vessel was added 280 mL of 90% acetone-water prepared from 252 mL of acetone and 28 mL of water. The mixture was stirred at heating in a water bath and dissolved under reflux (water bath; 65° C.). After the dissolution was confirmed, the water bath was cooled to 50° C. After addition of 35 mL of water, 140 mg of seed crystals [a small amount of crystals of 3-(2-cyanophenyl)-5-(2-pyridyl)-1-phenyl-1,2-dihydropyridin-2-one hydrate] was added to the vessel at an internal temperature of 50° C. A thermostat bath was used to cool the mixture to −20° C. at a cooling rate of about 35° C./hour. After stirring the mixture at −20° C. for 1 hour, the precipitated solids were collected by filtration and dried under reduced pressure (at an external temperature of 30° C. for 1 hour and then at 60° C. for 2 hours). The obtained dried powders (6.3 g) were transferred to a Petri dish and were allowed to stand in the atmosphere for 17 hours (humidity before standing: 55.4%; humidity after overnight standing: 61.6%) to give 6.2 g of crystals of 3-(2-cyanophenyl)-5-(2-pyridyl)-1-phenyl-1,2-dihydropyridin-2-one hydrate.

$^1$H NMR (400 MHz, DMSO-$d_6$): δ 8.61-8.57 (m, 1H), 8.53 (d, 1H), 8.47 (d, 1H), 8.01 (d, 1H), 7.92 (d, 1H), 7.83 (ddd, 1H), 7.78 (ddd, 1H), 7.73-7.71 (d-like, 1H), 7.61-7.48 (m, 6H), 7.30 (dd, 1H).

Analysis of Water Content (Karl Fisher's Method)
3.9% w/w; calculated for $C_{23}H_{15}N_3O·¾H_2O$ 3.72% w/w Example 6

Production of Anhydrous Crystals of 3-(2-cyanophenyl)-5-(2-pyridyl)-1-phenyl-1,2-dihydropyridin-2-one (Anhydrous Crystal Form V)

A 500 mL-vessel was charged with 9 g of 3-(2-cyanophenyl)-5-(2-pyridyl)-1-phenyl-1,2-dihydropyridin-2-one (crystal form of the hydrate). Acetone (360 mL) was added to the vessel and the mixture was stirred at heating under reflux at 70° C. in a water bath.

After dissolution, the mixture was filtrated by suction and the filtrate was concentrated at 75° C. under normal pressure to solidify. After the solids were finely ground in a mortar, an acetone-water solution prepared from 216 mL of acetone and 54 mL of water was added to the solids.

The mixture was stirred at heating under reflux (at 75° C. in a water bath). After dissolution, the mixture was additional stirred at heating under reflux for 2 hours and 40 minutes. Subsequently, the temperature of the water bath for the mixture (external temperature) was cooled to room temperature at a cooling rate of 10° C./hour, and it was stirred at room temperature for 16 hours.

The precipitates in the reaction mixture were suction-filtrated and then dried under reduced pressure (an external temperature of 20° C. for 40 minutes and then at 60° C. for 3 hours) to give 7.2 g of the anhydrous crystals of 3-(2-cyanophenyl)-5-(2-pyridyl)-1-phenyl-1,2-dihydropyridin-2-one.

$^1$H NMR (400 MHz, DMSO-$d_6$): δ 8.61-8.57 (m, 1H), 8.53 (d, 1H), 8.47 (d, 1H), 8.01 (d, 1H), 7.92 (dd, 1H), 7.83 (ddd, 1H), 7.78 (ddd, 111), 7.72 (dd, 1H), 7.61-7.48 (m, 6H), 7.31-7.28 (m, 1H).

Example 7

Production of the Anhydrous Crystals of 3-(2-cyanophenyl)-5-(2-pyridyl)-1-phenyl-1,2-dihydropyridin-2-one (Anhydrous Crystal Form I)

A 1-L vessel was charged with 8 g of 3-(2-cyanophenyl)-5-(2-pyridyl)-1-phenyl-1,2-dihydropyridin-2-one (Hydrate). Ethyl acetate (480 mL) was added to the vessel and the mixture was stirred at heating under reflux (in an oil bath) to effect dissolution. Heating was stopped and the stirring was allowed to continue while the vessel was in the oil bath (under gradual cooling). At the point that the internal temperature reached 50.9° C., 0.2 g of seed crystals [3-(2-cyanophenyl)-5-(2-pyridyl)-1-phenyl-1,2-dihydropyridin-2-one (anhydrous crystal)] was added to the mixture. Subsequently, stirring continued until the internal temperature reached 31.3° C. The mixture was stirred for additional 2 hours in an ice bath. The precipitated crystals were collected by filtration and dried under aeration (50° C./18 hours) to give 5.8 g of anhydrous crystals of 3-(2-cyanophenyl)-5-(2-pyridyl)-1-phenyl-1,2-dihydropyridin-2-one.

$^1$H NMR (400 MHz, DMSO-$d_6$): δ 8.58 (d, 1H), 8.53 (d, 1H), 8.47 (d, 1H), 8.01 (d, 1H), 7.93 (d, 1H), 7.83 (ddd, 1H), 7.78 (d, 1H), 7.72 (d, 1H), 7.61-7.48 (m, 6H), 7.32-7.27 (m, 1H).

Experiment Test 1
Physical Stability in Mixing-Operation in the Presence of Water or Water-Ethanol (1:1) Mixed Solution
(1) Operation Procedure About 150 mg of respective crystals are placed in an agate mortar, and the mixing operation is carried out at room temperature for a few minutes while the dropwise addition of water (or water-ethanol (1:1) mixed solution) continues. Subsequently, respective crystals are dried at about 60° C. for 2 to 3 hours.

(2) Results

The powder X-ray diffraction analysis showed that the crystals obtained in Reference Example 1 underwent a change in crystal form during the mixing operation in the presence of water or a water-ethanol (1:1) mixed solution and the same crystal form as that obtained in Example 7 increased in quantity.

The powder X-ray diffraction analysis showed that the respective crystals obtained in Example 5, Example 6 and Example 7 displayed no change in crystal form and they were physically stable in the presence of water or a water-ethanol (1:1) mixed solution.

Experiment Test 2
Influence of Change in Temperature and Humidity on Hydrate Crystal
(1) Apparatus Rigaku X-ray DTA system: MINT-2000 manufactured by Rigaku Corporation (2) Operation Procedure Crystals obtained in Example 5 (Hydrate crystal) were ground in a mortar and then sampled on a 13-mm diameter glass plate. Measurement was carried out under the conditions below.

X-ray in use: CuKα ray
Tube voltage: 40 kV
Tube current: 200 mA
Divergent slit: ½ deg
Receiving slit: 0.3 mm
Scattering slit: ½ deg
Scanning speed: 2°/min
Scanning step: 0.01°
Scanning range (2θ): 5 to 40°

Measurement temperature was changed as follows in turn and powder X-ray diffraction patterns were measured at the respective temperatures in sequence: 30→40→50→60→70→80→100→70→60→50→40 and 30° C.

(3) Results 1

Figure 11:
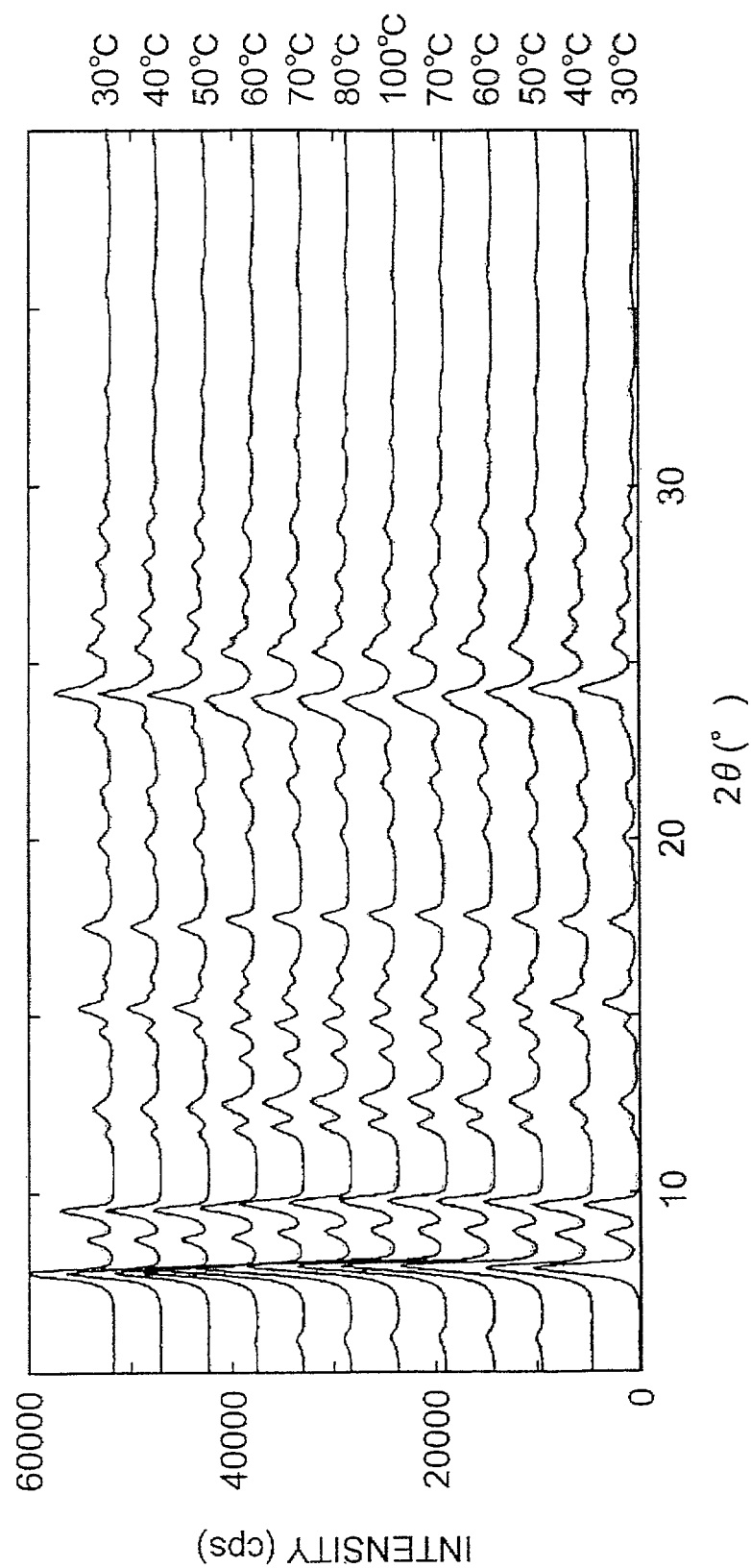
FIG. 11 shows powder X-ray diffraction patterns of Hydrate crystal at various temperatures.

FIG. 11 shows powder X-ray diffraction patterns of Hydrate at respective temperatures above. The changes in the powder X-ray diffraction patterns revealed that the crystals of Example 5 (Hydrate crystal) transform to the same crystals as crystals of Example E1 (Anhydrous crystal form III) at about 60° C. or more, and return again to Hydrate when the temperature was lowered.

(4) Results 2

Measurement humidity was changed as follows in turn and powder X-ray diffraction patterns were measured at the respective humidities in sequence: 4→5→10→15→20→50→90→50→15→5% RH (relative humidity).

Figure 12:
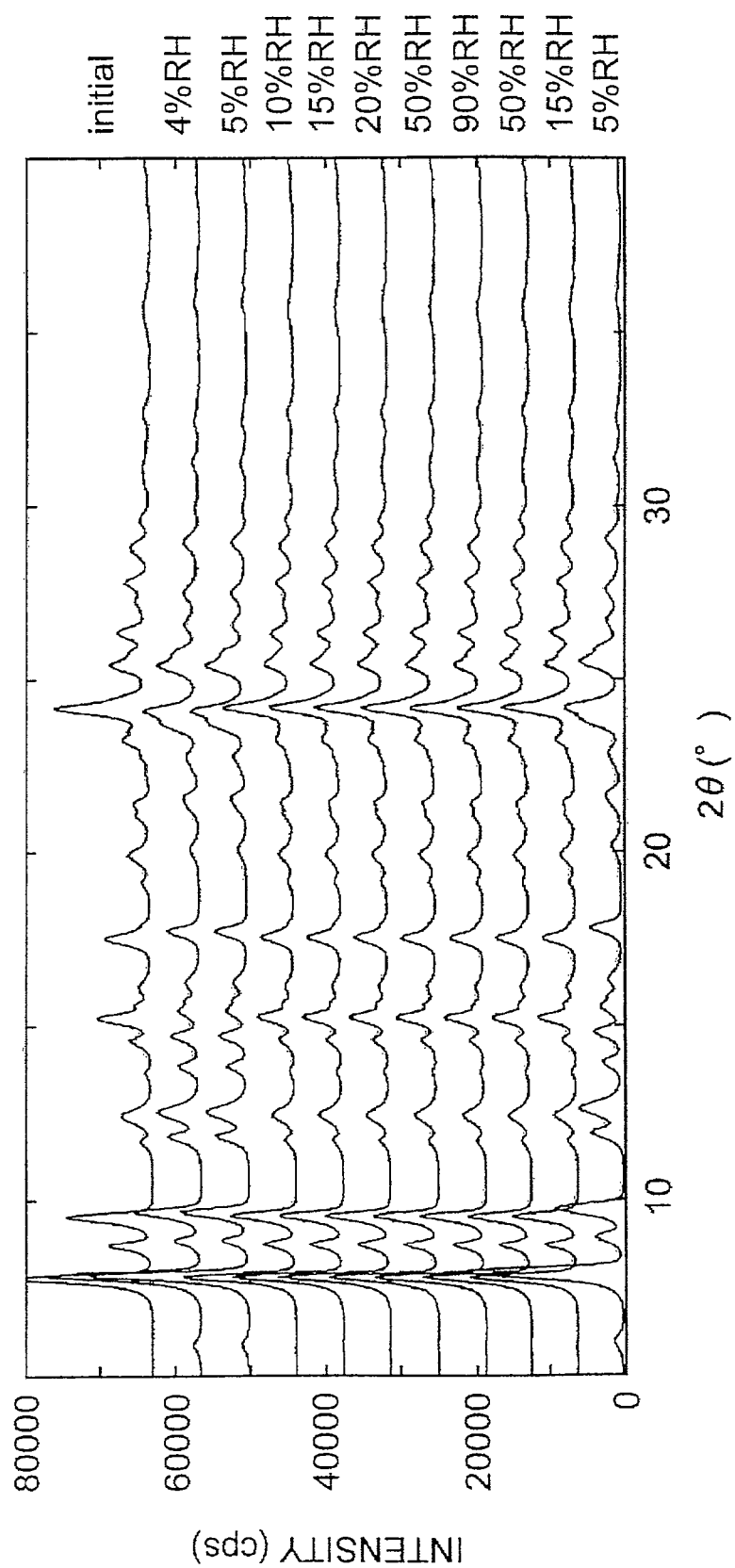
FIG. 12 shows powder X-ray diffraction patterns of Hydrate crystal under various relative humidities.

FIG. 12 shows powder X-ray diffraction patterns of Hydrate crystal at respective humidities above. From changes in the powder X-ray diffraction patterns, reversible patterns of Hydrate crystal and Anhydrous crystal form III were observed under the humidity of more and less of about 10% RH. It is confirmed that the crystals of Example 5 (Hydrate crystal) change to Anhydrous crystal form III under the humidity of about 10% RH or less, and stay Hydrate crystal under the humidity of about 10% RH or more.

These experiments about the influence of changes in temperature and humidity on Hydrate crystal, and Example 4 revealed that the state of the precipitates before the air drying was the same crystals as those of Example E1 (Anhydrous crystal form III) or a mixture of Anhydrous crystal form DI and Hydrate crystal, which is a useful intermediate for the production of Hydrate crystal.

Experiment Test 3
Minimum Ignition Energy and Lower Explosion Concentration Limit
(1) Operation Procedure An appropriate amount of Hydrate crystal corresponding to a concentration was uniformly put on sample dish of blown-up type dust explosion test apparatus. 50 kPa of air was compressed in a 1.3 L pressure tank, and the air was introduced into a glass cylinder by opening of a solenoid operated valve to form dust clouds. A discharge electrode was supplied with energy after 0.1 seconds after the opening of the solenoid operated valve. The criterion of ignition is an arrival of flame at an ignition mark set 100 mm above the discharge electrode.
(2) Measurement Conditions for Lower Explosion Concentration Limit
  Temperature of the measurement room: 24° C.
  Humidity: 49%
  Popping pressure of compressed air: 50 kPa
  Ignition start time: 0.1 sec
  Repetition of ignition test: 5 times
  Ignition discharge energy: 10 J
(3) Measurement Conditions for Minimum Ignition Energy
  Temperature of the measurement room: 24° C.
  Humidity: 49%
  Popping pressure of compressed air: 50 kPa
  Ignition start time: 0.1 sec
  Repetition of ignition test: 10 times
(4) Apparatus
  Blown-up type dust explosion test apparatus (Environmental Technology Co., Ltd. DES-10)
(5) Results
  Lower Explosion Concentration Limit: 160-170 g/m$^3$
  Minimum Ignition Energy: 50-100 mJ
  Dust concentration: 1250 g/m$^3$ Experiment Test 4
Chargeability
(1) Operation Procedure About 1 g of respective compounds is weighed into a weighing bottle (diameter of 35 mm) A stirring bar [fluoroplastic (tetrafluoroethylene resin) coating; 20 mm] is placed in the bottle and after the lid is in place, the powders are stirred for 30 minutes. The lid is opened at the same time that stirring is stopped; and the static potential of the powder is measured using a static potential measuring instrument.
(2) Apparatus
  STATIRON-DZ3 manufactured by Shishido Electrostatic, Ltd.

Figure 2:
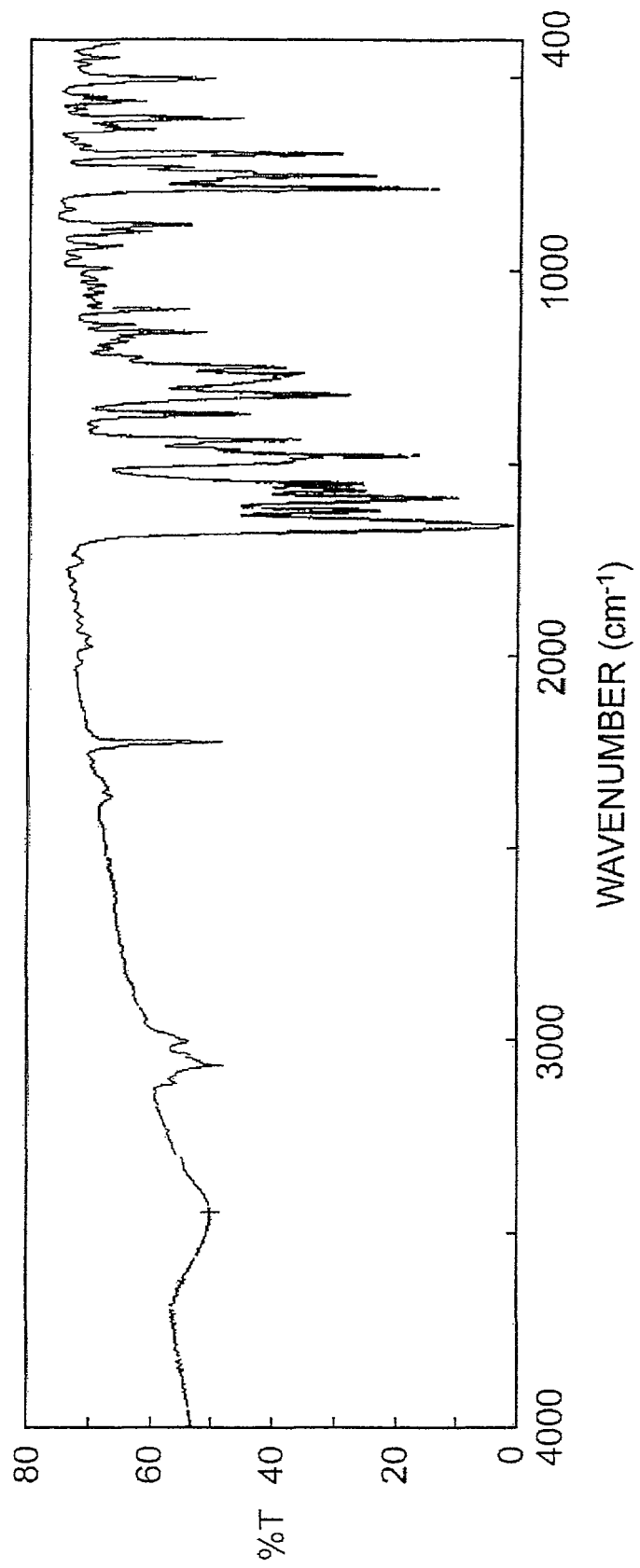
FIG. 2 shows an infrared spectrum (KBr method) of the crystals obtained in Example 6.

(3) Results
  Crystals of Reference Example 1: 70-100 V
  Crystals of Example 5: 0 V
Experiment Test 5
Measurement of Infrared Spectra
(1) Operation Procedure Infrared spectrum of the crystals obtained in Example 5 was measured under the measurement conditions described below according to the potassium bromide disk method for infrared spectrum measurement as described in General Tests in the Japanese Pharmacopoeia.
(2) Apparatus
  FT/IR-620 manufactured by JASCO Corporation
(3) Conditions for Measurements
  Measuring range: 4000-400 cm$^{-1}$
  Resolution: 4 cm$^{-1}$
  Integration number: 36
  Scanning speed: 2 mm/sec
(4) Results FIG. 1 shows an infrared spectrum of the crystals obtained in Example 5 (KBr method) and FIG. 2 shows an infrared spectrum of the crystals obtained in Example 6 (KBr method).

Table 2 shows the wavenumbers (cm$^{-1}$) and transmittances (%) of the absorption peaks for the crystals obtained in Example 5.

Table 3 shows the wavenumbers (cm$^{-1}$) and transmittances (%) of the absorption peaks for the crystals obtained in Example 6.

TABLE 2

| PEAK NUMBER | WAVENUMBER (cm$^{-1}$) | % T |
|---|---|---|
| 1 | 3406.64 | 46.3391 |
| 2 | 2217.74 | 56.7481 |
| 3 | 1661.37 | 6.6427 |
| 4 | 1619.91 | 40.6542 |
| 5 | 1588.09 | 25.9365 |
| 6 | 1566.88 | 40.1575 |
| 7 | 1550.49 | 43.7805 |
| 8 | 1482.03 | 35.2300 |
| 9 | 1434.78 | 48.9801 |
| 10 | 1369.21 | 56.9666 |
| 11 | 1318.11 | 46.9775 |
| 12 | 1282.43 | 47.1779 |
| 13 | 1249.65 | 56.0844 |
| 14 | 1157.08 | 60.4468 |
| 15 | 1099.23 | 60.6605 |
| 16 | 899.63 | 68.4385 |
| 17 | 879.38 | 62.5325 |
| 18 | 784.89 | 24.6745 |
| 19 | 751.14 | 35.0064 |
| 20 | 730.89 | 57.4603 |
| 21 | 697.14 | 39.9667 |
| 22 | 606.50 | 56.3319 |
| 23 | 557.33 | 62.4188 |
| 24 | 505.26 | 58.3988 |

TABLE 3

| PEAK NUMBER | WAVENUMBER (cm$^{-1}$) | % T |
|---|---|---|
| 1 | 3447.13 | 50.2836 |
| 2 | 3066.26 | 49.6530 |
| 3 | 2221.59 | 49.7414 |
| 4 | 1657.52 | 1.0035 |
| 5 | 1618.95 | 24.2890 |
| 6 | 1585.20 | 11.2133 |
| 7 | 1565.92 | 26.5039 |
| 8 | 1549.52 | 26.7864 |
| 9 | 1476.24 | 17.5093 |

TABLE 3-continued

| PEAK NUMBER | WAVENUMBER (cm$^{-1}$) | % T |
|---|---|---|
| 10 | 1434.78 | 36.9734 |
| 11 | 1368.25 | 45.1127 |
| 12 | 1318.11 | 29.2805 |
| 13 | 1266.04 | 36.7269 |
| 14 | 1247.72 | 39.2277 |
| 15 | 1157.08 | 52.6189 |
| 16 | 1135.87 | 64.5032 |
| 17 | 1097.30 | 55.2787 |
| 18 | 933.38 | 66.5017 |
| 19 | 896.74 | 61.6446 |
| 20 | 879.38 | 55.0085 |
| 21 | 785.85 | 14.4121 |
| 22 | 753.07 | 24.8345 |
| 23 | 729.92 | 54.7682 |
| 24 | 694.25 | 30.5167 |
| 25 | 630.61 | 61.1148 |
| 26 | 603.61 | 46.5267 |
| 27 | 556.36 | 62.4971 |
| 28 | 501.40 | 51.0929 |
| 29 | 443.55 | 67.0781 |

Experiment Test 6
Measurement of Powder X-Ray Diffraction Pattern
(1) Operation Procedure Powder X-ray diffraction patterns of the crystals obtained in the respective Examples were measured under the measurement conditions described below according to the powder X-ray diffraction measurement method as described in General Tests in the Japanese Pharmacopoeia.

(2) Apparatus
Rigaku X-ray DTA system: RINT-2000 manufactured by Rigaku Corporation (3) Operation Procedure A sample was ground in a mortar and then sampled on a 13-mm diameter glass plate. Measurement was carried out under the conditions below.
X-ray in use: CuKα ray
Tube voltage: 40 kV
Tube current: 200 mA
Divergent slit: ½ deg
Receiving slit: 0.3 mm
Scattering slit: ½ deg
Scanning speed: 1°/min
Scanning step: 0.01°
Scanning range (2θ): 5 to 40°

(4) Results

Figure 3:
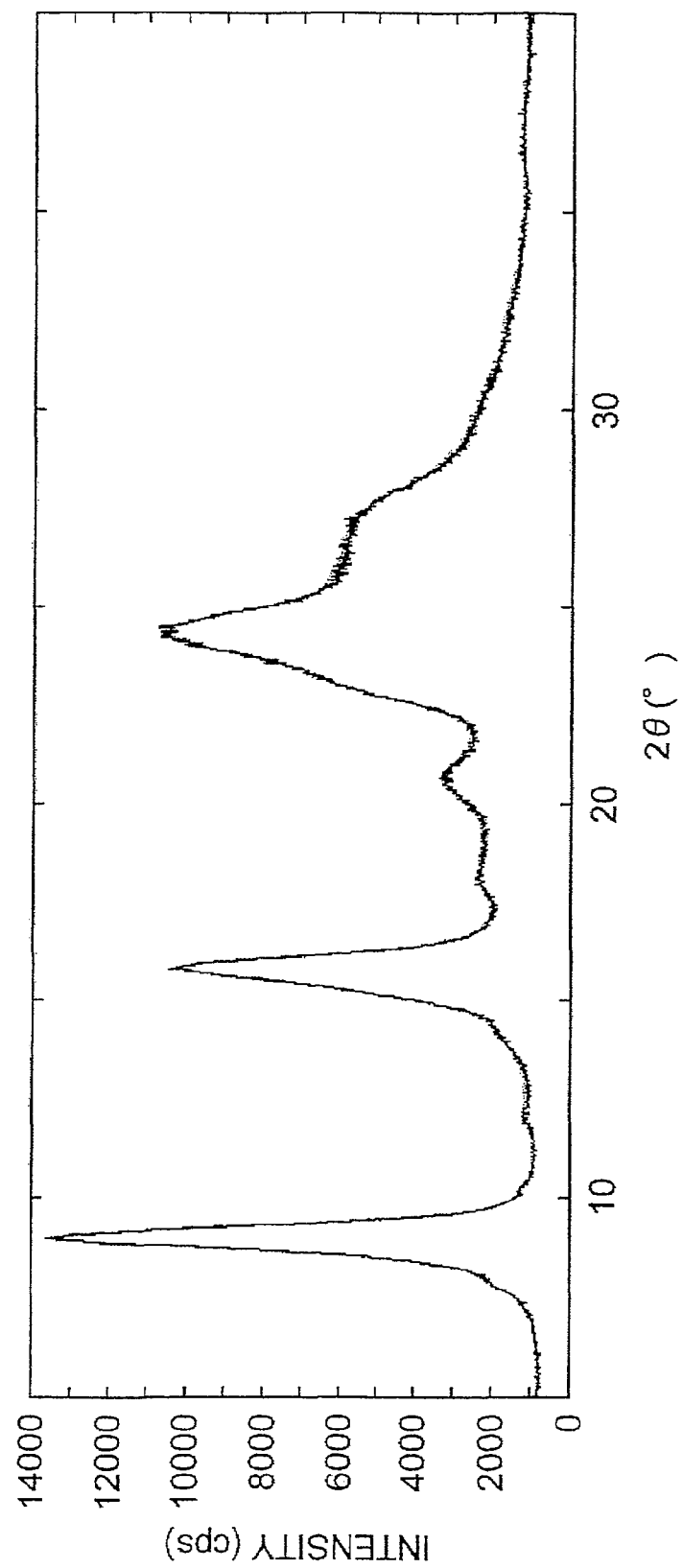
FIG. 3 shows a powder X-ray diffraction pattern of the crystals obtained in Reference Example 1.
Figure 4:
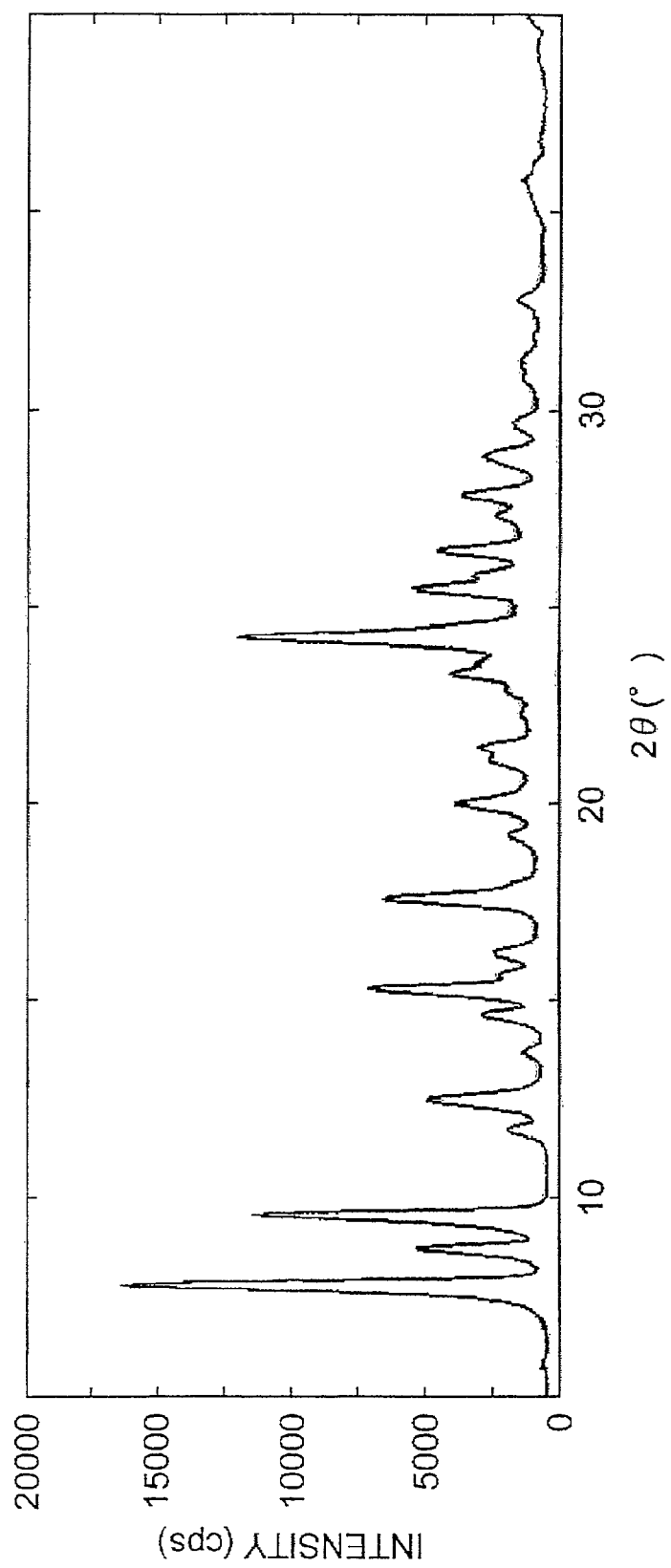
FIG. 4 shows a powder X-ray diffraction pattern of the crystals obtained in Example 5.
Figure 5:
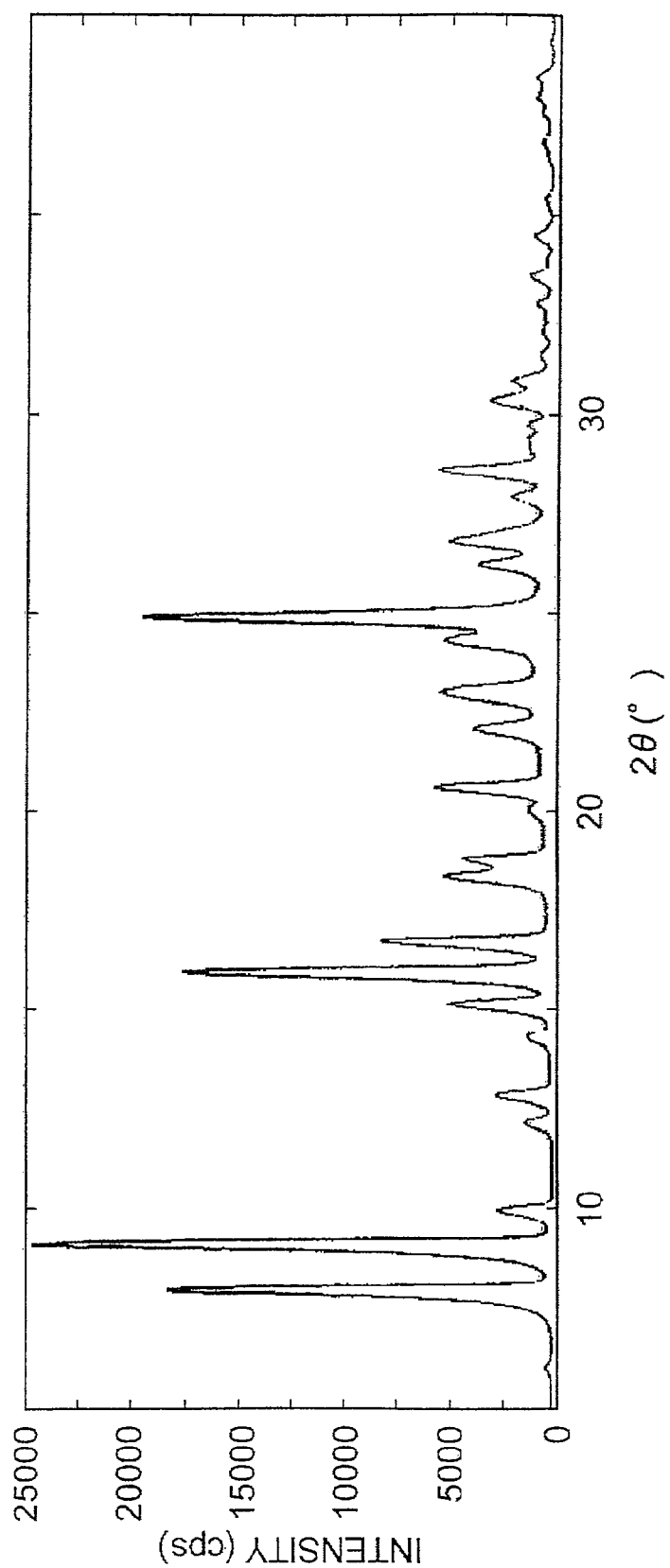
FIG. 5 shows a powder X-ray diffraction pattern of the crystals obtained in Example 6.
Figure 6:
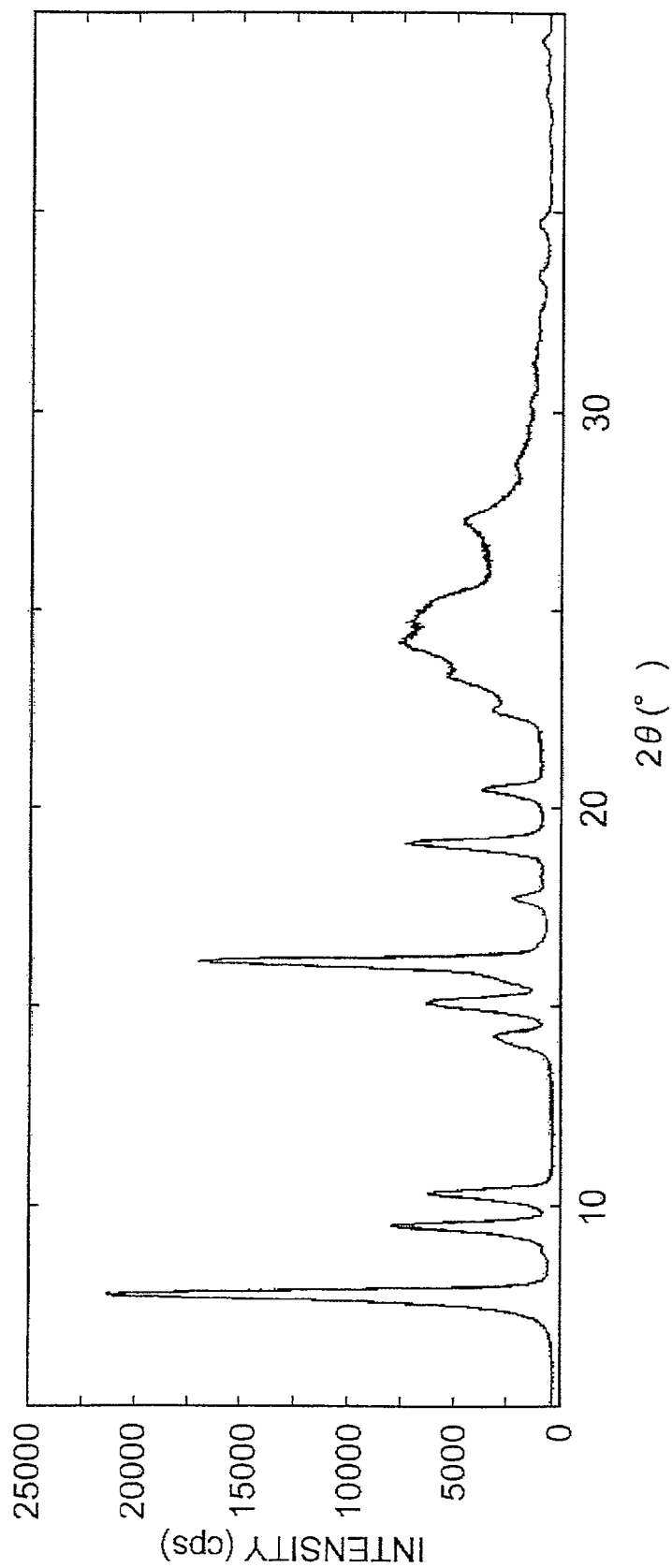
FIG. 6 shows a powder X-ray diffraction pattern of the crystals obtained in Example 7.

FIG. 3 shows a powder X-ray diffraction pattern of the crystals obtained in Reference Example 1, FIG. 4 shows a powder X-ray diffraction pattern of the crystals obtained in Example 5, FIG. 5 shows a powder X-ray diffraction pattern of the crystals obtained in Example 6, and FIG. 6 shows a powder X-ray diffraction pattern of the crystals obtained in Example 7.

Table 4 shows the peaks and their intensities at diffraction angles (2θ) for the crystals obtained in Reference Example 1, Table 5 shows the peaks and their intensities at diffraction angles (2θ) for the crystals obtained in Example 5, Table 6 shows the peaks and their intensities at diffraction angles (2θ) for the crystals obtained in Example 6, and Table 7 shows the peaks and their intensities at diffraction angles (2θ) for the crystals obtained in Example 7.

Based on FIG. 4 and Table 5 that represent the powder X-ray diffraction pattern of the crystals obtained in Example 5, it can be found that the powder X-ray diffraction pattern of the crystals obtained in Example 5 provides a characteristic peak having a diffraction angle (2θ) of about 12.5°.

This suggests that the crystals obtained in Reference Example 1 do not contain the same crystal form as do the crystals obtained in Example 5, since FIG. 3 and Table 4 that represent the powder X-ray diffraction pattern of the crystals obtained in Reference Example 1 does not provide the peak having a diffraction angle (2θ) of about 12.5.

Example E1

Anhydrous Form III

With respect to the crystals of 3-(2-cyanophenyl)-5-(2-pyridyl)-1-phenyl-1,2-dihydropyridin-2-one hydrate, the powder X-ray diffraction pattern was measured under the conditions similar to those described above. However, the measurement was conducted at a scanning speed of 2°/min under heating conditions in the vicinity of 110° C.

Figure 7:
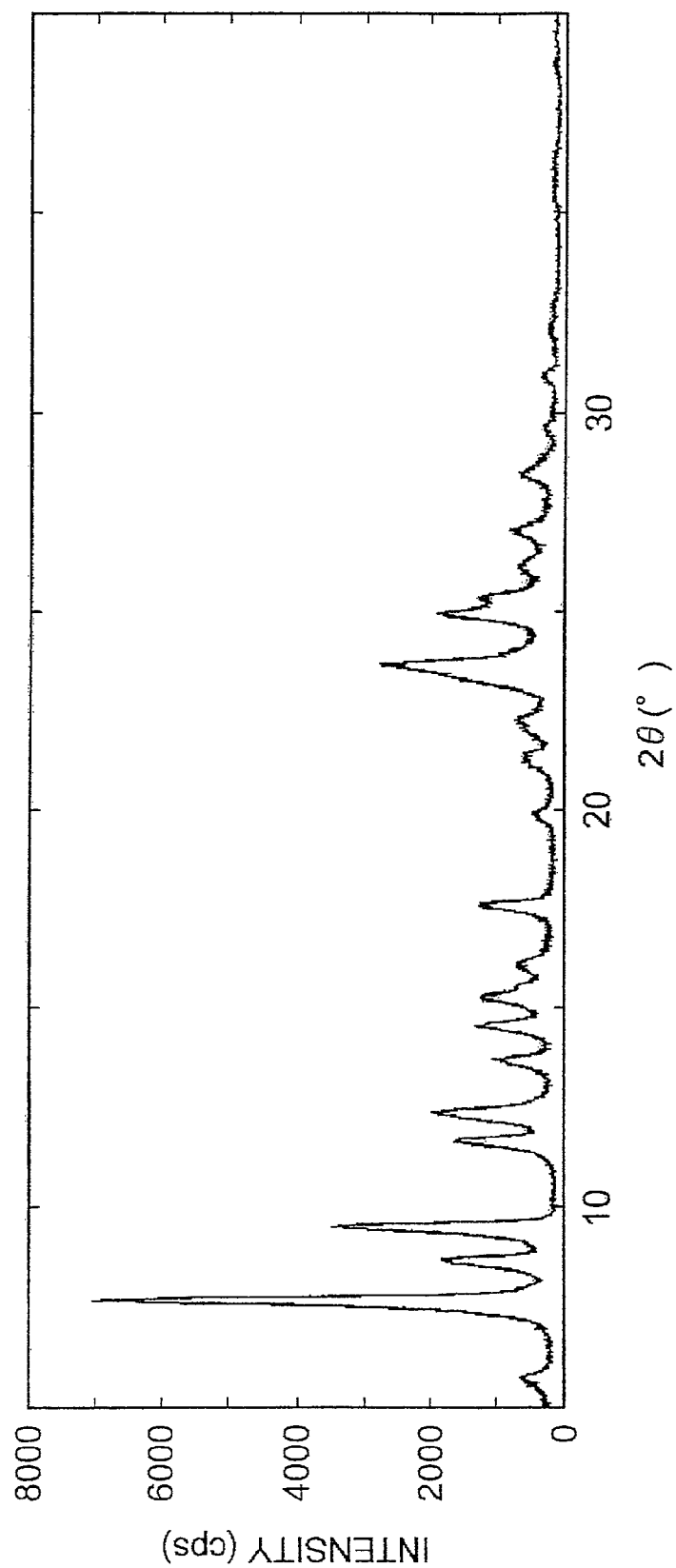
FIG. 7 shows a powder X-ray diffraction pattern of the crystals as described in Example E1.

FIG. 7 shows the powder X-ray diffraction pattern, and Table 8 shows the peaks and the intensity of diffraction angles (2θ±0.2°) for the crystals.

TABLE 4

| PEAK NUMBER | 2θ | HALF WIDTH | d-VALUE | INTENSITY | RELATIVE INTENSITY |
|---|---|---|---|---|---|
| 1 | 9.010 | 0.588 | 9.8067 | 13370 | 100 |
| 2 | 15.850 | 0.682 | 5.5867 | 10137 | 76 |
| 3 | 24.390 | 0.847 | 3.6465 | 10672 | 80 |

TABLE 5

| PEAK NUMBER | 2θ | HALF WIDTH | d-VALUE | INTENSITY | RELATIVE INTENSITY |
|---|---|---|---|---|---|
| 1 | 7.780 | 0.259 | 11.3542 | 16328 | 100 |
| 2 | 8.700 | 0.247 | 10.1555 | 5298 | 32 |
| 3 | 9.520 | 0.282 | 9.2825 | 11203 | 69 |
| 4 | 12.450 | 0.365 | 7.1037 | 4845 | 30 |
| 5 | 14.590 | 0.282 | 6.0663 | 2872 | 18 |
| 6 | 15.240 | 0.329 | 5.8090 | 7037 | 43 |
| 7 | 15.600 | 0.188 | 5.6757 | 2162 | 13 |
| 8 | 16.180 | 0.282 | 5.4735 | 2358 | 14 |
| 9 | 17.540 | 0.341 | 5.0521 | 6268 | 38 |
| 10 | 19.980 | 0.318 | 4.4403 | 3823 | 23 |
| 11 | 21.040 | 0.247 | 4.2189 | 2430 | 15 |
| 12 | 21.420 | 0.271 | 4.1449 | 2708 | 17 |
| 13 | 23.260 | 0.282 | 3.8210 | 3838 | 24 |
| 14 | 24.190 | 0.294 | 3.6762 | 12030 | 74 |
| 15 | 25.440 | 0.282 | 3.4983 | 5205 | 32 |
| 16 | 25.820 | 0.188 | 3.4477 | 2953 | 18 |
| 17 | 26.430 | 0.294 | 3.3695 | 4488 | 27 |
| 18 | 27.310 | 0.259 | 3.2629 | 2295 | 14 |
| 19 | 27.860 | 0.341 | 3.1997 | 3567 | 22 |
| 20 | 28.870 | 0.294 | 3.0900 | 2645 | 16 |

TABLE 6

| PEAK NUMBER | 2θ | HALF WIDTH | d-VALUE | INTENSITY | RELATIVE INTENSITY |
|---|---|---|---|---|---|
| 1 | 8.000 | 0.259 | 11.0424 | 18318 | 76 |
| 2 | 9.160 | 0.259 | 9.6465 | 24045 | 100 |
| 3 | 10.000 | 0.294 | 8.8380 | 3002 | 12 |
| 4 | 12.870 | 0.259 | 6.8728 | 2838 | 12 |
| 5 | 15.140 | 0.247 | 5.8471 | 5210 | 22 |
| 6 | 15.950 | 0.282 | 5.5519 | 17707 | 74 |
| 7 | 16.720 | 0.306 | 5.2979 | 8272 | 34 |
| 8 | 18.370 | 0.271 | 4.8256 | 5460 | 23 |
| 9 | 18.820 | 0.235 | 4.7113 | 4523 | 19 |
| 10 | 20.650 | 0.259 | 4.2977 | 5878 | 24 |
| 11 | 22.150 | 0.318 | 4.0099 | 3967 | 16 |

TABLE 6-continued

| PEAK NUMBER | 2θ | HALF WIDTH | d-VALUE | INTENSITY | RELATIVE INTENSITY |
|---|---|---|---|---|---|
| 12 | 23.100 | 0.224 | 3.8471 | 5378 | 22 |
| 13 | 24.320 | 0.365 | 3.6568 | 5333 | 22 |
| 14 | 24.930 | 0.306 | 3.5687 | 19343 | 80 |
| 15 | 26.280 | 0.271 | 3.3884 | 3737 | 16 |
| 16 | 26.860 | 0.282 | 3.3165 | 5103 | 21 |
| 17 | 28.010 | 0.306 | 3.1829 | 2182 | 9 |
| 18 | 28.660 | 0.294 | 3.1122 | 5767 | 24 |
| 19 | 30.410 | 0.259 | 2.9369 | 3333 | 14 |
| 20 | 30.900 | 0.282 | 2.8915 | 2363 | 10 |

TABLE 7

| PEAK NUMBER | 2θ | HALF WIDTH | d-VALUE | INTENSITY | RELATIVE INTENSITY |
|---|---|---|---|---|---|
| 1 | 7.780 | 0.235 | 11.3542 | 20997 | 100 |
| 2 | 9.450 | 0.259 | 9.3511 | 7993 | 38 |
| 3 | 10.270 | 0.247 | 8.6062 | 6090 | 29 |
| 4 | 14.240 | 0.247 | 6.2146 | 3092 | 15 |
| 5 | 15.060 | 0.353 | 5.8780 | 6283 | 30 |
| 6 | 16.070 | 0.271 | 5.5107 | 16920 | 81 |
| 7 | 19.080 | 0.294 | 4.6476 | 7162 | 34 |
| 8 | 20.450 | 0.259 | 4.3393 | 3658 | 17 |
| 9 | 22.440 | 0.259 | 3.9588 | 3212 | 15 |
| 10 | 23.300 | 0.176 | 3.8145 | 5342 | 25 |
| 11 | 24.150 | 0.094 | 3.6822 | 7478 | 36 |
| 12 | 27.310 | 0.106 | 3.2629 | 4648 | 22 |

TABLE 8

| PEAK NUMBER | 2θ | HALF WIDTH | d-VALUE | INTENSITY | RELATIVE INTENSITY |
|---|---|---|---|---|---|
| 1 | 5.700 | 0.235 | 15.4919 | 557 | 8 |
| 2 | 7.660 | 0.224 | 11.5318 | 6780 | 100 |
| 3 | 8.650 | 0.247 | 10.2141 | 1813 | 27 |
| 4 | 9.490 | 0.259 | 9.3118 | 3490 | 51 |
| 5 | 11.640 | 0.259 | 7.5962 | 1603 | 24 |
| 6 | 12.350 | 0.282 | 7.1610 | 1817 | 27 |
| 7 | 13.690 | 0.271 | 6.4630 | 1057 | 16 |
| 8 | 14.550 | 0.200 | 6.0828 | 1247 | 18 |
| 9 | 15.240 | 0.271 | 5.8090 | 1230 | 18 |
| 10 | 15.530 | 0.118 | 5.7011 | 717 | 11 |
| 11 | 16.110 | 0.141 | 5.4972 | 650 | 10 |
| 12 | 17.590 | 0.306 | 5.0378 | 1237 | 18 |
| 13 | 19.940 | 0.141 | 4.4491 | 417 | 6 |
| 14 | 21.450 | 0.141 | 4.1392 | 540 | 8 |
| 15 | 22.300 | 0.271 | 3.9833 | 750 | 11 |
| 16 | 23.700 | 0.247 | 3.7511 | 2560 | 38 |
| 17 | 24.960 | 0.235 | 3.5645 | 1783 | 26 |
| 18 | 25.420 | 0.106 | 3.5010 | 1173 | 17 |
| 19 | 26.150 | 0.259 | 3.4049 | 720 | 11 |
| 20 | 27.030 | — | 3.2960 | 703 | 10 |
| 21 | 28.500 | 0.200 | 3.1293 | 670 | 10 |

Figure 8:
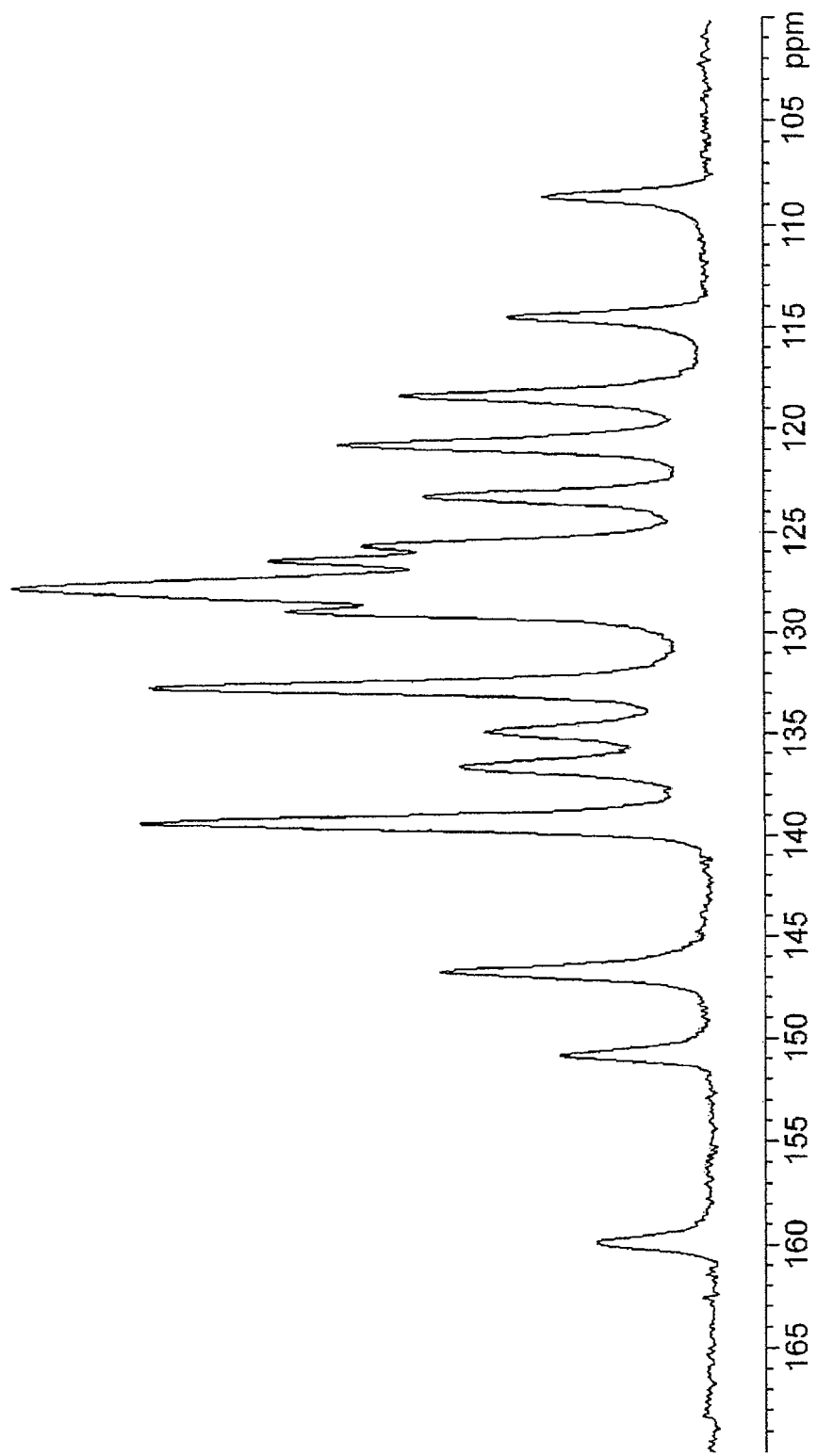
FIG. 8 shows a $^{13}$C Solid State Nuclear Magnetic Resonance (NMR) spectrum of the crystals obtained in Example 5.
Figure 9:
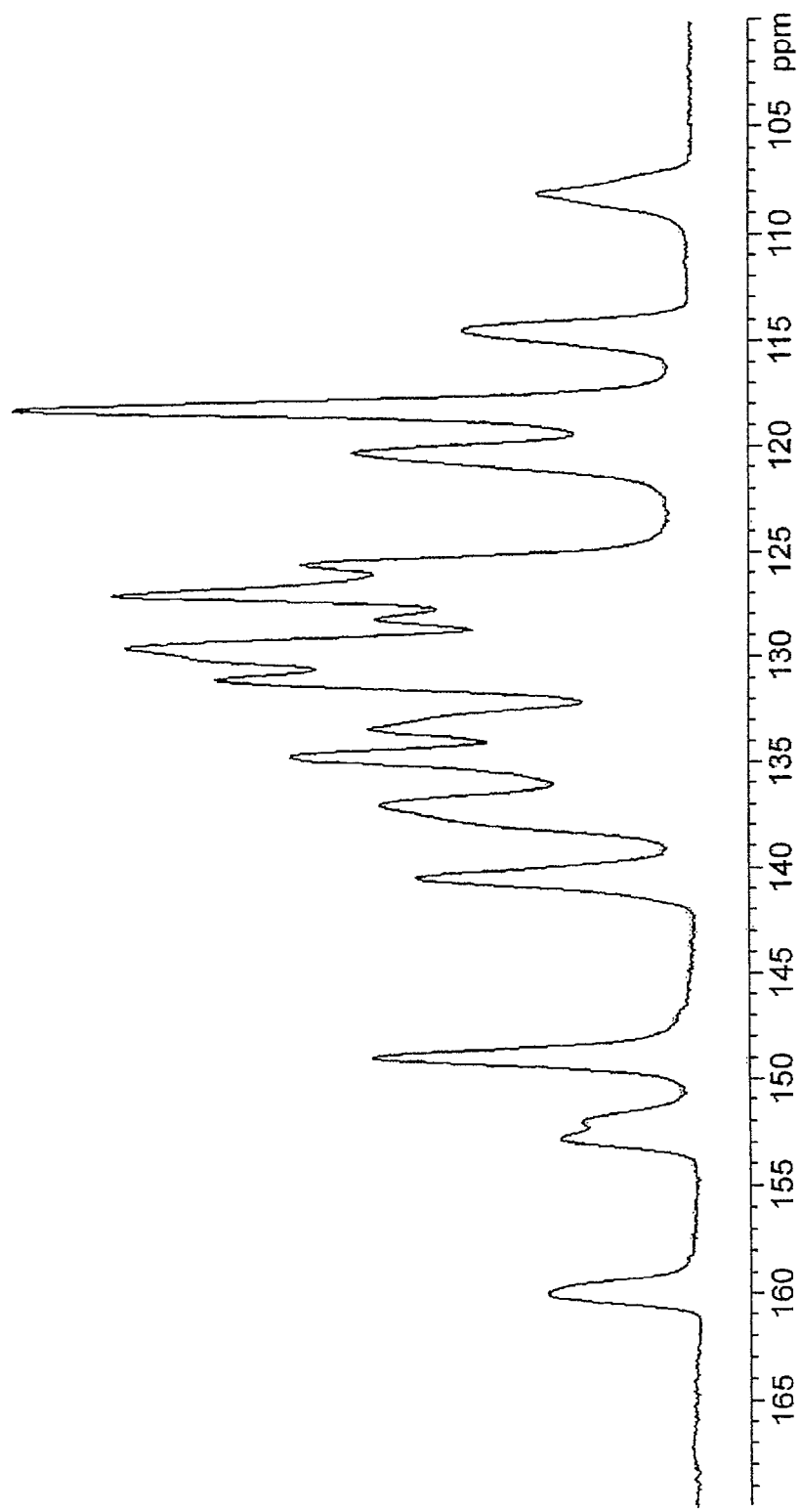
FIG. 9 shows a $^{13}$C Solid State NMR spectrum of the crystals obtained in Example 7.
Figure 10:
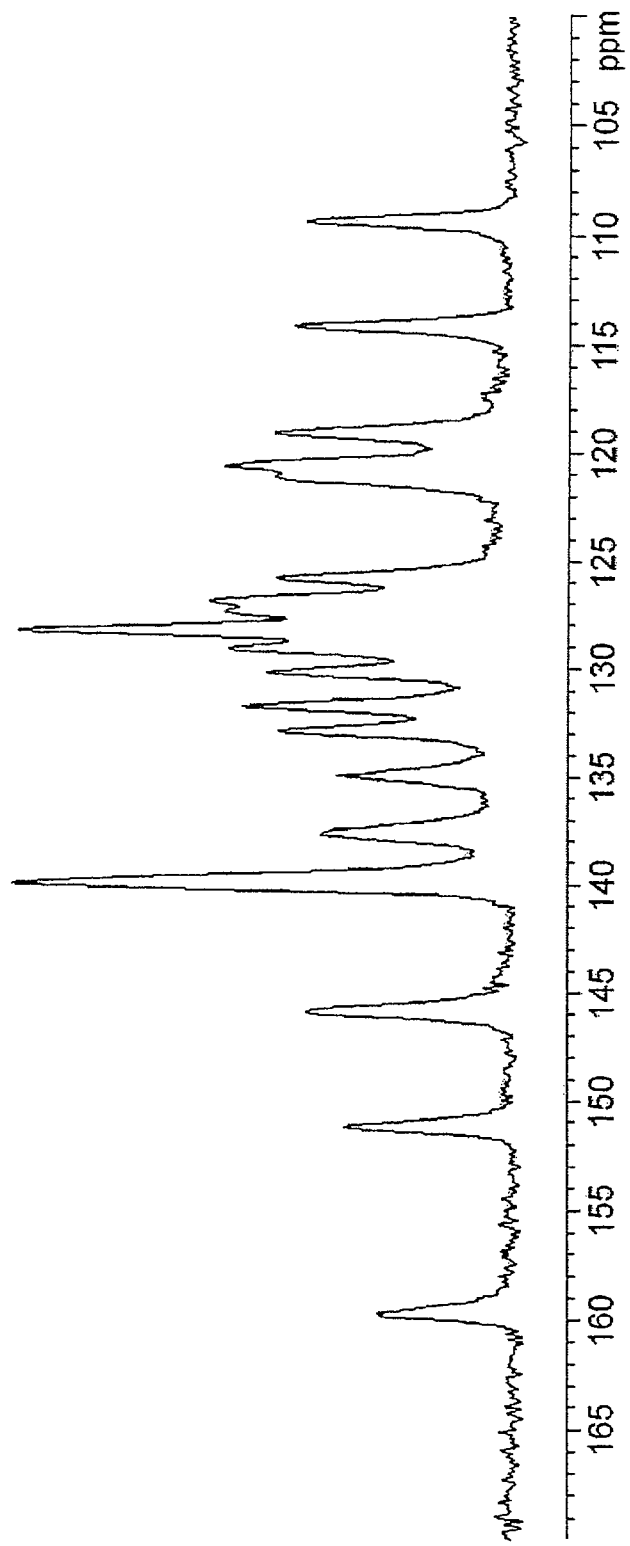
FIG. 10 shows a $^{13}$C Solid State NMR spectrum of the crystals obtained in Example 6.

Experiment Test 7
Measurement of $^{13}$C Solid State NMR Spectrum
(1) Operation Procedure
$^{13}$C Solid State NMR spectra were measured for the crystals obtained in Examples 5, 6 and 7 under the following conditions.
Measurement temperature: room temperature (~22° C.)
Standard compound: carbonyl carbon of glycine (external standard: 176.03 ppm)
Measurement nucleus: $^{13}$C (100.6248425 MHz)
Pulse-repetition time: 50 sec for Examples 6 and 7
5 sec for Example B1
Pulse mode: CP/TOSS measurement (2) Results
FIG. 8 shows a $^{13}$C Solid State NMR spectrum of the crystals obtained in Example 5, and the chemical shifts are summarized in Table 9. FIG. 9 shows a $^{13}$C Solid State NMR spectrum of the crystals obtained in Example 7, and the chemical shifts are summarized in Table 10. FIG. 10 shows a $^{13}$C Solid State NMR spectrum of the crystals obtained in Example 6, and the chemical shifts are summarized in Table 11.

TABLE 9

| Chemical Shift(ppm) |
|---|
| 159.8 |
| 150.8 |
| 146.7 |
| 139.4 |
| 136.6 |
| 134.9 |
| 132.7 |
| 129.0 |
| 127.8 |
| 126.5 |
| 125.8 |
| 123.3 |
| 120.8 |
| 118.4 |
| 114.6 |
| 108.8 |

TABLE 10

| Chemical Shift(ppm) |
|---|
| 160.0 |
| 152.8 |
| 152.0 |
| 149.0 |
| 140.5 |
| 137.0 |
| 134.7 |
| 133.4 |
| 131.0 |
| 129.5 |
| 128.2 |
| 127.0 |
| 125.6 |
| 120.3 |
| 118.2 |
| 114.6 |
| 108.2 |

TABLE 11

| Chemical Shift(ppm) |
|---|
| 159.7 |
| 151.2 |
| 145.9 |
| 139.9 |
| 137.7 |
| 134.9 |
| 132.8 |
| 131.7 |
| 130.1 |
| 129.0 |
| 128.2 |
| 127.3 |
| 126.8 |
| 125.8 |
| 121.1 |
| 120.6 |

TABLE 11-continued

| Chemical Shift(ppm) |
|---|
| 119.1 |
| 114.2 |
| 109.4 |

As explained in detail herein above, according to the present invention, a compound represented by formula (IR) may be industrially produced in good yield and high purity by reacting a compound represented by formula (I) with a compound represented by formula (II) in the presence of a palladium compound, a copper compound, a phosphorus compound and a base.

The crystal forms of the present invention have preferable properties and are suitable for use as an active ingredient of therapeutic or prophylactic agents for neurodegenerative diseases or the like.

What is claimed:

1. A crystal of 3-(2-cyanophenyl)-5-(2-pyridyl)-1-phenyl-1,2-dihydropyridin-2-one hydrate having a diffraction peak at a diffraction angle (2θ±0.2°) of 8.7° in a powder X-ray diffraction.

2. A crystal of 3-(2-cyanophenyl)-5-(2-pyridyl)-1-phenyl-1,2-dihydropyridin-2-one hydrate having a diffraction peak at a diffraction angle (2θ±0.2°) of 12.5° in a powder X-ray diffraction.

3. A crystal of 3-(2-cyanophenyl)-5-(2-pyridyl)-1-phenyl-1,2-dihydropyridin-2-one hydrate having diffraction peaks at diffraction angles (2θ±0.2°) of 8.7° and 12.5° in a powder X-ray diffraction.

4. A crystal of 3-(2-cyanophenyl)-5-(2-pyridyl)-1-phenyl-1,2-dihydropyridin-2-one hydrate having an absorption peak at a wavenumber of 1588±1 cm$^{-1}$ in an infrared absorption spectrum (KBr method).

5. A crystal of 3-(2-cyanophenyl)-5-(2-pyridyl)-1-phenyl-1,2-dihydropyridin-2-one hydrate having absorption peaks at wavenumbers of 1588±1 cm$^{-1}$ and 751±1 cm$^{-1}$ in an infrared absorption spectrum (KBr method).

6. A crystal of 3-(2-cyanophenyl)-5-(2-pyridyl)-1-phenyl-1,2-dihydropyridin-2-one hydrate having peaks at chemical shifts of around 146.7 ppm and around 123.3 ppm in a $^{13}$C Solid State Nuclear Magnetic Resonance spectrum.

7. A process for producing a crystal of 3-(2-cyanophenyl)-5-(2-pyridyl)-1-phenyl-1,2-dihydropyridin-2-one hydrate, the process comprising the step of crystallizing 3-(2-cyanophenyl)-5-(2-pyridyl)-1-phenyl-1,2-dihydropyridin-2-one with an aid of one or two crystallization solvents selected from the group consisting of an alcoholic solvent, an alkylketone solvent, and water, wherein the 3-(2-cyanophenyl)-5-(2-pyridyl)-1-phenyl-1,2-dihydropyridin-2-one hydrate has (a) a diffraction peak at a diffraction angle (2θ±0.2°) of 8.7° in a powder X-ray diffraction, (b) a diffraction peak at a diffraction angle (2θ±0.2°) of 12.5° in a powder X-ray diffraction, (c) diffraction peaks at diffraction angles (2θ±0.2°) of 8.7° and 12.5° in a powder X-ray diffraction, (d) an absorption peak at a wavenumber of 1588±1 cm$^{-1}$ in an infrared absorption spectrum (KBr method), (e) absorption peaks at wavenumbers of 1588±1 cm$^{-1}$ and 751±1 cm$^{-1}$ in an infrared absorption spectrum (KBr method) or, (f) peaks at chemical shifts of around 146.7 ppm and around 123.3 ppm in a $^{13}$C Solid State Nuclear Magnetic Resonance spectrum, (g) diffraction peaks at diffraction angles (2θ±0.2°) of 7.78°, 8.70° and 24.19° in a powder X-ray diffraction, (h) diffraction peaks at diffraction angles (2θ±0.2°) of 7.78°, 8.70°, 9.52°, 12.45° and 24.19° in a powder X-ray diffraction, (i) diffraction peaks at diffraction angles (2θ±0.2°) of 7.78°, 8.70°, 9.52°, 12.45°, 15.24°, 17.54°, 23.26°, 24.19°, 25.44° and 26.43° in a powder X-ray diffraction, (j) diffraction peaks at diffraction angles (2θ±0.2° of 7.78°, 8.70°, 9.52°, 12.45°, 14.59°, 15.24°, 15.60°, 16.18°, 17.54°, 19.98°, 21.04°, 21.42°, 23.26°, 24.19°, 25.44°, 25.82°, 26.43°, 27.31°, 27.86° and 28.87° in a powder X-ray diffraction, (k) absorption peaks at wavenumbers of 1661.37±1 cm$^{-1}$, 1482.03±1 cm$^{-1}$, 1282.43±1 cm$^{-1}$, 899.63±1 cm$^{-1}$ and 784.89±1 cm$^{-1}$ in an infrared absorption spectrum (KBr method), (l) absorption peaks at wavenumbers of 3406.64±1 cm$^{-1}$, 2217.74±1 cm$^{-1}$, 1661.37±1 cm$^{-1}$, 1619.91±1 cm$^{-1}$, 1588.09±1 cm$^{-1}$, 1566.88±1 cm$^{-1}$, 1550.49±1 cm$^{-1}$, 1482.03±1 cm$^{-1}$, 1434.78±1 cm$^{-1}$, 1369.21±1 cm$^{-1}$, 1318.11±1 cm$^{-1}$, 1282.43±1 cm$^{-1}$, 1249.65±1 cm$^{-1}$, 1157.08±1 cm$^{-1}$, 1099.23±1 cm$^{-1}$, 899.63±1 cm$^{-1}$, 879.38±1 cm$^{-1}$, 784.89±1 cm$^{-1}$, 751.14±1 cm$^{-1}$, 730.89±1 cm$^{-1}$, 697.14±1 cm$^{-1}$, 606.50±1 cm$^{-1}$, 557.33±1 cm$^{-1}$ and 505.26±1 cm$^{-1}$ in an infrared absorption spectrum (KBr method), (m) peaks at chemical shifts of around 146.7 ppm, around 139.4 ppm, around 132.7 ppm, around 123.3 ppm, around 120.8 ppm and around 118.4 ppm in a $^{13}$C Solid State Nuclear Magnetic Resonance spectrum, (n) peaks at chemical shifts of around 159.8 ppm, around 150.8 ppm, around 146.7 ppm, around 139.4 ppm, around 136.6 ppm, around 134.9 ppm, around 132.7 ppm, around 129.0 ppm, around 127.8 ppm, around 126.5 ppm, around 125.8 ppm, around 123.3 ppm, around 120.8 ppm, around 118.4 ppm, around 114.6 ppm and around 108.8 ppm in a $^{13}$C Solid State Nuclear Magnetic Resonance spectrum, (o) a powder X-ray diffraction pattern shown in FIG. 4, (p) an infrared spectrum (KBr method) shown in FIG. 1 or (q) a $^{13}$C Solid State NMR spectrum shown in FIG. 8.

8. The process according to claim 7, wherein the crystallization solvent is a mixed solvent of acetone and water.

9. The process according to claim 7, wherein the crystallization solvent is a mixed solvent of acetone and water with a volume ratio of 37:3 to 24:16.

10. The process according to claim 7, wherein the crystallization is carried out at a temperature of 60 to −30° C.

11. The process according to claim 7 comprising the steps of heating a solution of 3-(2-cyanophenyl)-5-(2-pyridyl)-1-phenyl-1,2-dihydropyridin-2-one dissolved in the crystallization solvent at a temperature of 50° C. or more and thereafter cooling the solution to a temperature of 10 to −20° C. at a cooling rate of 40 to 5° C. per hour.

12. The process according to claim 7, wherein the crystallization solvent is used in a volume ratio of 10- to 50-fold (v/w) based on the weight of 3-(2-cyanophenyl)-5-(2-pyridyl)-1-phenyl-1,2-dihydropyridin-2-one.

13. The process according to claim 7, wherein seed crystals are added at 60° C. or less.

14. The process according to claim 7, wherein the crystals are dried under reduced pressure after the crystallization.

15. The process according to claim 7, wherein the crystals are allowed to stand in the atmosphere after the crystallization and the drying under reduced pressure.

16. A crystal of 3-(2-cyanophenyl)-5-(2-pyridyl)-1-phenyl-1,2-dihydropyridin-2-one hydrate having diffraction peaks at diffraction angles (2θ±0.2°) of 7.78°, 8.70° and 24.19° in a powder X-ray diffraction.

17. A crystal of 3-(2-cyanophenyl)-5-(2-pyridyl)-1-phenyl-1,2-dihydropyridin-2-one hydrate having diffraction peaks at diffraction angles (2θ±0.2°) of 7.78°, 8.70°, 9.52°, 12.45° and 24.19° in a powder X-ray diffraction.

18. A crystal of 3-(2-cyanophenyl)-5-(2-pyridyl)-1-phenyl-1,2-dihydropyridin-2-one hydrate having diffraction peaks at diffraction angles (2θ±0.2°) of 7.78°, 8.70°, 9.52°, 12.45°, 15.24°, 17.54°, 23.26°, 24.19°, 25.44° and 26.43° in a powder X-ray diffraction.

19. A crystal of 3-(2-cyanophenyl)-5-(2-pyridyl)-1-phenyl-1,2-dihydropyridin-2-one hydrate having diffraction peaks at diffraction angles (2θ±0.2°) of 7.78°, 8.70°, 9.52°, 12.45°, 14.59°, 15.24°, 15.60°, 16.18°, 17.54°, 19.98°, 21.04°, 21.42°, 23.26°, 24.19°, 25.44°, 25.82°, 26.43°, 27.31°, 27.86° and 28.87° in a powder X-ray diffraction.

20. A crystal of 3-(2-cyanophenyl)-5-(2-pyridyl)-1-phenyl-1,2-dihydropyridin-2-one hydrate having absorption peaks at wavenumbers of 1661.37±1 $cm^{-1}$, 1482.03±1 $cm^{-1}$, 1282.43±1 $cm^{-1}$, 899.63±1 $cm^{-1}$ and 784.89±1 $cm^{-1}$ in an infrared absorption spectrum (KBr method).

21. A crystal of 3-(2-cyanophenyl)-5-(2-pyridyl)-1-phenyl-1,2-dihydropyridin-2-one hydrate having absorption peaks at wavenumbers of 3406.64±1 $cm^{-1}$, 2217.74±1 $cm^{-1}$, 1661.37±1 $cm^{-1}$, 1619.91±1 $cm^{-1}$, 1588.09±1 $cm^{-1}$, 1566.88±1 $cm^{-1}$, 1550.49±1 $cm^{-1}$, 1482.03±1 $cm^{-1}$, 1434.78±1 $cm^{-1}$, 1369.21±1 $cm^{-1}$, 1318.11±1 $cm^{-1}$, 1282.43±1 $cm^{-1}$, 1249.65±1 $cm^{-1}$, 1157.08±1 $cm^{-1}$, 1099.23±1 $cm^{-1}$, 899.63±1 $cm^{-1}$, 879.38±1 $cm^{-1}$, 784.89±1 $cm^{-1}$, 751.14±1 $cm^{-1}$, 730.89±1 $cm^{-1}$, 697.14±1 $cm^{-1}$, 606.50±1 $cm^{-1}$, 557.33±1 $cm^{-1}$ and 505.26±1 $cm^{-1}$ in an infrared absorption spectrum (KBr method).

22. A crystal of 3-(2-cyanophenyl)-5-(2-pyridyl)-1-phenyl-1,2-dihydropyridin-2-one hydrate having peaks at chemical shifts of around 146.7 ppm, around 139.4 ppm, around 132.7 ppm, around 123.3 ppm, around 120.8 ppm and around 118.4 ppm in a $^{13}$C Solid State Nuclear Magnetic Resonance spectrum.

23. A crystal of 3-(2-cyanophenyl)-5-(2-pyridyl)-1-phenyl-1,2-dihydropyridin-2-one hydrate having peaks at chemical shifts of around 159.8 ppm, around 150.8 ppm, around 146.7 ppm, around 139.4 ppm, around 136.6 ppm, around 134.9 ppm, around 132.7 ppm, around 129.0 ppm, around 127.8 ppm, around 126.5 ppm, around 125.8 ppm, around 123.3 ppm, around 120.8 ppm, around 118.4 ppm, around 114.6 ppm and around 108.8 ppm in a $^{13}$C Solid State Nuclear Magnetic Resonance spectrum.

24. A crystal of 3-(2-cyanophenyl)-5-(2-pyridyl)-1-phenyl-1,2-dihydropyridin-2-one hydrate having a powder X-ray diffraction pattern shown in FIG. 4.

25. A crystal of 3-(2-cyanophenyl)-5-(2-pyridyl)-1-phenyl-1,2-dihydropyridin-2-one hydrate having an infrared spectrum (KBr method) shown in FIG. 1.

26. A crystal of 3-(2-cyanophenyl)-5-(2-pyridyl)-1-phenyl-1,2-dihydropyridin-2-one hydrate having a $^{13}$C Solid State NMR spectrum shown in FIG. 8.

* * * * *